(12) United States Patent
Li et al.

(10) Patent No.: US 9,133,195 B2
(45) Date of Patent: Sep. 15, 2015

(54) QUATERNARY AMMONIUM SALT COMPOUNDS OF SPIROCYCLOPIPERAZINES, PREPARATION METHODS AND USES THEREOF

(75) Inventors: Runtao Li, Beijing (CN); Qi Sun, Beijing (CN); Jia Ye, Beijing (CN); Caiqin Yue, Beijing (CN); Xin Wang, Beijing (CN); Zemei Ge, Beijing (CN); Changling Li, Beijing (CN); Tieming Cheng, Beijing (CN)

(73) Assignee: Peking University, Beijing (CN)

( * ) Notice: Subject to any disclaimer, the term of this patent is extended or adjusted under 35 U.S.C. 154(b) by 339 days.

(21) Appl. No.: 12/305,174

(22) PCT Filed: Jun. 15, 2007

(86) PCT No.: PCT/CN2007/001887
§ 371 (c)(1),
(2), (4) Date: Apr. 20, 2009

(87) PCT Pub. No.: WO2007/147346
PCT Pub. Date: Dec. 27, 2007

(65) Prior Publication Data
US 2009/0325929 A1    Dec. 31, 2009

(30) Foreign Application Priority Data

Jun. 16, 2006 (CN) .......................... 2006 1 0086917

(51) Int. Cl.
| | | |
|---|---|---|
| *A61K 31/55* | (2006.01) | |
| *C07D 471/10* | (2006.01) | |
| *A61K 31/438* | (2006.01) | |
| *A61K 31/5386* | (2006.01) | |
| *C07D 498/10* | (2006.01) | |
| *C07D 487/10* | (2006.01) | |
| *C07D 513/10* | (2006.01) | |
| *C07D 519/00* | (2006.01) | |

(52) U.S. Cl.
CPC ............ *C07D 471/10* (2013.01); *C07D 487/10* (2013.01); *C07D 498/10* (2013.01); *C07D 513/10* (2013.01); *C07D 519/00* (2013.01)

(58) Field of Classification Search
None
See application file for complete search history.

(56) References Cited

U.S. PATENT DOCUMENTS

| 3,630,680 A | 12/1971 | Rittersdorf et al. |
| 3,711,459 A * | 1/1973 | Hegar et al. .................. 534/605 |
| 2006/0017424 A1 | 1/2006 | Wood et al. |

FOREIGN PATENT DOCUMENTS

| CN | 1344717 A | 4/2002 |
| JP | 57024384 A | 2/1982 |
| JP | 4234387 A | 8/1992 |
| JP | 5097846 A | 4/1993 |
| JP | 2001131149 A | 5/2001 |
| WO | WO 2006/055503 A2 | 5/2006 |

OTHER PUBLICATIONS

Light et al. In Journal of the American Pharmaceutical Association (1957), 46, 279-287.*
Nutley et al. In British Journal of Cancer (2005) 93, 1011-1018.*
Yue et al. In Pharmacology, Biochemistry and Behavior 86, 643-650 (2007).*

(Continued)

*Primary Examiner* — Dennis Heyer
(74) *Attorney, Agent, or Firm* — Scott A. McCollister; Fay Sharpe LLP

(57) ABSTRACT

Compounds represented by general formula (I), their stereoisomers, tautomers, derivatives, prodrugs or pharmaceutically acceptable salts, and their preparation methods or uses for the manufacture of a medicament of analgesics. In which $R_1$ is selected from H, substituted or unsubstituted phenyl, or substituted or unsubstituted heteroaryl; A is a bond, or saturated or unsaturated straight-chain or branched-chain hydrocarbon radical; $R_2$, $R_3$ are each independently hydrogen or methyl, which linked with any position of spirocyclo-structure; n and m are each independently integer between 0-2, do not represent 0 at the same time; B and D are each independently $C_1$-$C_3$ straight-chain or branched-chain alkylene; Y is selected from —$CHR_4$—, O, S, —S(O)—, —$SO_2$—, —$NR_4$— and substituted or unsubstituted phenylene, in which $R_4$ represents H, $C_1$-$C_6$ saturated or unsaturated alkyl, methyl or ethyl substituted by substituted or unsubstituted aryl or heteroaryl; and X⁻ is pharmaceutical acceptable organic or inorganic anion. These compounds can be used as muscarine receptor (M-receptor) and/or nicotine acetylcholine receptor (N-receptor) agonist or antagonist. These compounds have good analgesic effect without side effect such as addiction.

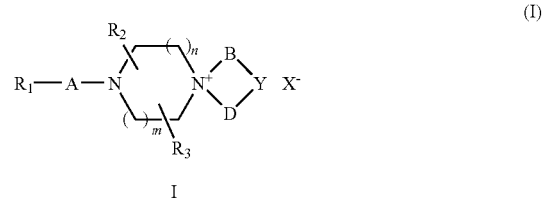

(I)

I

17 Claims, 3 Drawing Sheets

(56) References Cited

OTHER PUBLICATIONS

Unique Spirocyclopiperazinium Salt I: Synthesis and Structure—Activity Relationship of Spirocyclopiperazinium Salts as Analgesics, Feng Li Gao et al., Science Direct, Bioorganic & Medicinal Chemistry Letters 13 (2003), pp. 1535-1537, School of Pharmaceutical Sciences, Peking University, Beijing 100083, PR China, Received Jan. 10, 2003; accepted Feb. 17, 2003.

Unique Spirocyclopiperazinium Salt Part 2: Synthesis and Structure—Activity Relationship of Dispirocyclopiperazinium Salts as Analgesics, Xin Wang et al., Science Direct, Bioorganic & Medicinal Chemistry Letters 13 (2003), pp. 1729-1732, School of Pharmaceutical Sciences, Peking University, Beijing 100083, PR China, Received Jan. 10, 2003; accepted Mar. 1, 2003.

AN 1999:470679 CAPLUS Full-Text, DN 131:228607, TI Synthesis and pharmacological screening of some N-(4-substituted-piperazin-1-ylalkyl) -3, 4-pyrrolodicarboximides, AU Malinka, Wieslaw et al., CS Department of Chemistry of Drugs, Wroclaw University of Medicine, Wroclaw, 50-137, Pol., so Farmaco (1999), 54(6), 390-401, 2 pages.

AN 1991:583160 CAPLUS Full text, DN 115:183160, TI Synthesis and properties of 2H-2-(4-substituted-1-piperazinylalkyl)-4,6-dimethyl-3-oxo 2, 3-dihyroisothiazolo [5, 4-b]pyridines, AU Malinka, Wieslaw, CS Dep. Chem. Drugs, Sch. Med., Wroclaw, 50-137, Pol. SO Acta Poloniae Pharmaceutica (1990), 47(1-2), 51-6 CODEN: APPHAX; ISSN: 0001-6837, 2 pages.

AN 2005:490481 CAPLUS Full-text, DN 142:482060, TI Preparation of novel derivative of 3,4-pyrrolodicarboximide as analgesic, IN Malinka, Wieslaw; Kleinrok, Zdzislaw; Sieklucka-Dziuba, Maria; Rajtar-Cynke, Grayzna, PA Akademia Medyczna im. Piastow Slaskich we Wroclawiu, Pol. SO Pol., 4 pp., CODEN: POXXA7, 1 page.

Anna Sparatore et al., 2-{4-] (1)[4-(2-Methoxyphenyl)-l-piperazinyl]alkoxy]phenyl}-2H-benzotriazoles and their N-Oxides as Ligands for some 5-Hydroxytryptamine, Dopamine and Adrenergic Receptor Subtypes; May 8, 2000, pp. 2-6/E, Instituto di Chimica Farmaceutiica e Tossicologica, University of Milan, Viale Abruzzi, 42-20131 Milan and *Dipartimento di Scienze Farmaceutiche, University of Genoa, Viale Benedetto XV, 3, 16132, Genoa, IT.

Kikuo Ishzum et al., Succinimide Derivatives, II.[1)] Synthesis and Antipsychotic Activity of N-[4-[4-(1,2-Benzisothiazol-3-yl)-1-piperazinyl]butyl]-1,2-cis-ciclohexanedicarboximide (SM-9018) and Related Compounds [2,3)]; Sumitomo Pharmaceuticals Research Center, 3-1-98 Kasugadenaka, Konohana-ku, Dec. 1995, pp. 2-14/E, Osaka 554, JP.

Eugene L. Stogeyn, Antimalarials Related to 2-Bromo-4,5-dimethoxy-N,N'-bis(diethyl-aminoethyl)aniline. Piperazine Modifications[1,2], Essu Research and Engineering Company, Government Research Laboratory, Jun. 20, 1968, pp. 2-4/E, Linden, NJ.

Horst Bohme et al., Zur Gewinnung quartarer Imidazolidiniumsalze, Aus dem Pharmazeutisch-Chemischen Institut der Universitat Marburg/Lahn, Mar. 22, 1996, pp. 2-7/E.

Amos E. Light et al., Antiacetylcholine Activity of Piperazine Derivatives, Nov. 21, 1956, pp. 2-10/E. Wellcome Research Laboratories, Tuckahoe, NY.

* cited by examiner

QUATERNARY AMMONIUM SALT COMPOUNDS OF SPIROCYCLOPIPERAZINES, PREPARATION METHODS AND USES THEREOF

FIELD OF THE INVENTION

The present invention relates to the agonists or antagonists of muscarine receptor (M-receptor) and/or nicotine acetylcholine receptor (N-receptor) agonist or antagonist, especially relates to a quaternary ammonium salt compounds of spirocyclopiperazines with analgesic activity, their preparation methods and uses.

BACKGROUND ART

Pain, which is a common disease in clinic, which is divided into three types: physical pain, inflammatory pain and neuralgia. At present, the analgesic drugs used in clinic mainly includes two categories, namely non-steroidal anti-inflammatory drugs (NSAIDs) and opiates.

Non-steroidal anti-inflammatory drugs (NSAIDs) are widely used to treat acute and chronic pain. They also can be used as the adjuvant reagents of the opiates. Commonly used non-steroidal anti-inflammatory drugs include: Aspirin, Ibuprofen, Indomethacin, Diclofenac, Ketorolac and Acetaminophen. Unfortunately, NSAIDs show some side-effects, such as stimulation to gastrointestinal tract and ulcers.

In clinic, if non-steroidal anti-inflammatory drugs can't relieve the pain totally, they would be used in combination with opiates. Commonly used opioids such as Morphine and Codeine can treat moderate to severe pains. Although opioids are potent analgesic effect, their clinical applications are strictly restricted because of their severe side effects, such as addiction, tolerance and respiratory depression.

Recently, the inventors disclosed a quaternary ammonium salt compounds of piperazines represented by Formula I~IV in Chinese patent application CN 01142111.8, which are novel compounds with potent analgesic effect and had no NSAIDs- or opiate-like side-effects. Their structures are showed below:

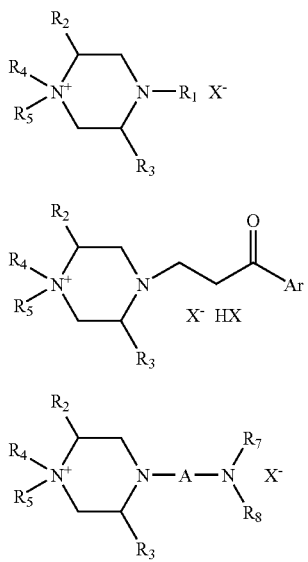

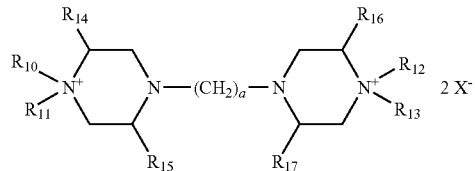

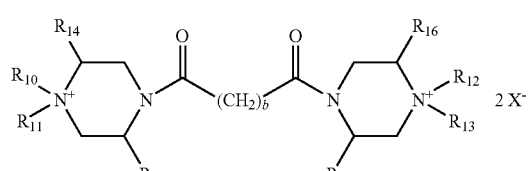

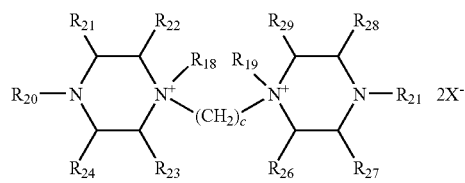

Base on the patent application mentioned above, in the present invention, we further discovered a series of novel quaternary ammonium salt compounds of piperazines with spirocyclo-structure, which has good analgesia function and no addiction.

DETAILED DESCRIPTION OF THE INVENTION

The object of this invention is to provide a series of novel quaternary ammonium salt of piperazines with spirocyclo-structure, which has side-effects such as excellent analgesic activities and no addiction.

Another object of this invention is to provide preparation methods and uses of those compounds mentioned above.

The present invention provides the following compounds represented by general formula I:

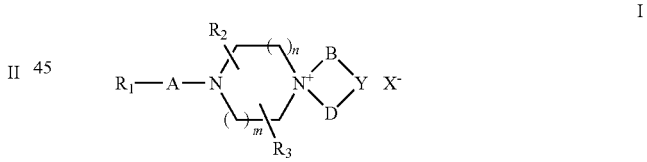

or their stereoisomers, tautomers, prodrugs, pharmaceutical acceptable salts, $R_1$ is substituted or unsubstituted phenyl, or substituted or unsubstituted heteroaryl;

A is a bond, or a saturated or unsaturated straight-chain, or branched-chain hydrocarbon radical;

$R_2$, $R_3$ are each independently hydrogen or methyl which is linked to any position of spirocyclo-structure;

n and m are each independently integer between 0-2, but m and n are not zero simultaneously;

B and D are each independently $C_1$-$C_3$ straight-chain or branched-chain alkylene;

Y is independently selected from a group consisting of —$CHR_4$—, O, S, —S(O)—, —$SO_2$—, —$NR_4$— and a substituted or unsubstituted phenylene, in which $R_4$ represents H, $C_1$-$C_6$ saturated or unsaturated alkyl, methyl or ethyl substituted by substituted or unsubstituted aryl or heteroaryl; and X⁻ is pharmaceutical acceptable organic or inorganic anion.

The term "substituted heteroaryl" herein refers to five- or six-numbered ring containing one to four hetero-atoms selected from N, O and S, preferably heteroaryl having one or more nitrogen atoms, for example, pyridyl, pyrazinyl, pyrazolyl, pyrimidinyl or pyridazinyl, more preferably pyridyl and pyridazinyl.

In the compound of the present invention, when $R_1$ is a substituted or unsubstituted phenyl, or substituted or unsubstituted heteroaryl, the term "substituted" refers to mono-substituted or poly-substituted, preferably substituted in para- or meso-position. "The substituent" mentioned above is selected from the group consisting of halogen, amino, hydroxy), cyano, nitro, alkyl, alkoxy or alkoxy carbonyl. The term "halogen" refers to fluorine, chlorine, bromine or iodine atom, preferably fluorine, chlorine or bromine atom; the term "alkyl" refers to a saturated hydrocarbonyl; the term "alkoxy" refers to a alkyl in which carbon atom is substituted by oxygen atom; preferably, for $R_1$ group, the said "alkyl" or "alkoxy" refers to straight-chain or branched-chain alkyl or alkoxy with 1-6 carbon atoms, more preferably straight-chain or branched-chain alkyl or alkoxy with 1-3 carbon atoms, especially preferably methyl, ethyl, propyl, methoxy or ethoxy. The term "alkoxy carbonyl" refers to the group with total carbon atoms of 2-6, preferably methoxycarbonyl or ethoxycarbonyl.

In the compound of the present invention, when A is a bond, or a saturated or unsaturated straight-chain or branched-chain, hydrocarbon radical, the term "hydrocarbon radical" refers to "chain hydrocarbon radical", including straight-chain or branched-chain alkylene, alkenylene or alkynylene; preferably straight-chain or branched-chain alkylene or alkenylene; more preferably straight-chain or branched-chain alkylene with 1 to 6 carbon atoms, for example, —CH$_2$—, —CH$_2$CH$_2$—, —CH(CH$_3$)—, —CH(CH$_3$)CH$_2$—, —CH$_2$CH(CH$_3$)CH$_3$— and —CH$_2$CH(CH$_2$CH$_3$)CH$_2$—, or straight-chain or branched-chain alkenylene with 1-3 carbon atoms in straight-chain part, such as —CH=CH—CH$_2$—, —C(CH$_3$)=CH—CH$_2$—, —CH=CH—CH(CH$_3$)—. A is especially preferably a bond, ethylene or —CH=CH—CH$_2$—.

In compound of the present invention, when $R_1$ is substituted or unsubstituted heteroaryl, A is preferably a bond.

In the compound of the present invention, "$R_1$-A-" preferably refers to p-methylphenyl, p-methoxyphenyl, p-nitrophenyl, m-nitrophenyl, p-chlorophenyl, o-methylphenyl, o-fluorophenyl, m-fluorophenyl, m-hydroxyphenyl, m-cyanophenyl, m-ethoxycarbonyl-phenyl, m-methoxycarbonyl-phenyl, m-aminophenyl, o-nitrophenyl, methylpyridyl, dimethylpyridyl, chloropyridyl (for example, 4-chloro-3-pyridyl-1-yl), methylpyridazinyl or chloropyridazinyl (for example, 4-chloro-2,3-pyridazin-1-yl).

In the compound of the present invention, the group B and D are each independently $C_1$-$C_3$ straight-chain or branched-chain alkylene, preferably —CH$_2$—, —CH$_2$CH$_2$—, —CH(CH$_3$)—, —CH$_2$CH$_2$CH$_2$— or —CH$_2$CH(CH$_3$)—.

In the compound of the present invention, Y is independently selected from a group consisting of —CHR$_4$—, O, S, —S(O)—, —SO$_2$—, —NR$_4$— and a substituted or unsubstituted phenylene, in which $R_4$ represents H, $C_1$-$C_6$, saturated or unsaturated alkyl, methyl or ethyl substituted by substituted or unsubstituted aryl or heteroaryl; preferably, $R_4$ represents H or straight-chain or branched-chain alkyl group with 1 to 3 carbon atoms, more preferably H, methyl or ethyl. When Y is a substituted or unsubstituted phenylene, preferably o-phenylene, the said substituted group is selected from a group consisting of —NO$_2$, -Me, —OMe, —CN, —CO$_2$H and —CO$_2$Et, etc. The most preferably, Y refers to —CH$_2$—, —CH(CH$_3$)—, —O—, —S—, —N(CH$_3$), —N(Et)-, or unsubstituted phenylene. Preferably, both m and n are 1.

The term "substituted" mentioned in the definition of Y group refers to mono- or poly-substituted, and the substituents have the same definition as described in $R_1$.

In the invention compound, X⁻ as counter ion is selected from pharmaceutical acceptable anion, especially the anion formed by the pharmaceutical acceptable acid, such as the inorganic acid, for example, hydrochloric acid, sulphuric acid, hydrobromic acid, hydrofluoric acid, hydriodic acid, nitric acid, sulfonic acid, phosphoric acid, etc; or the organic acid, for example, acetic acid, oxalic acid, citric acid, maleic acid, fumaric acid, succinic acid, malic acid, methylsulfonic acid or toluene sulfonic acid, etc. Preferably, X⁻ refers to halogen anion, especially chlorine or bromine anion.

Preferably, compounds in this invention are selected from the group consisting of:

3-(β-phenylethyl)-3,6-diazaspiro[5.5]undecane chloride;
3-methyl-9-(β-phenylethyl)-3,6,9-triazaspiro[5.5]undecane chloride;
3-(β-phenylethyl)-3,6-diazaspiro[5.5]-benzo[8,9]undecane chloride;
3-methyl-9-benzyl-3,6,9-triazaspiro[5.5]undecane chloride;
2,4-dimethyl-9-β-(p-nitrophenyl)ethyl-3-oxo-6,9-diazaspiro[5.5]undecane chloride;
3-methyl-9-(β-phenylethyl)-6,9-diazaspiro[5.5]undecane chloride;
2,4-dimethyl-9-β-(p-methoxyphenyl)ethyl-3-oxo-6,9-diazaspiro[5.5]undecane chloride;
2,4-dimethyl-9-β-(m-fluorophenyl)ethyl-3-oxo-6,9-diazaspiro[5.5]undecane chloride;
2,4-dimethyl-9-β-(m-nitrophenyl)ethyl-3-thio-6,9-diazaspiro[5.5]undecane chloride;
2,4-dimethyl-9-β-phenylethyl-3-oxo-6,9-diazaspiro[5.5]undecane chloride;
8-(4-chloro-2,3-pyridazinyl)-5,8-diazaspiro[4.5]decane chloride;
8-(β-phenylethyl)-5,8-diazaspiro[4.5]decane chloride;
3-(β-phenylethyl)-3,6-diazaspiro[5.6]dodecane chloride;
9-β-phenylethyl-3-oxo-6,9-diazaspiro[5.5]undecane chloride;
8-(p-nitrophenyl)-5,8-diazaspiro[4.5]decane bromide;
8-(m-nitrophenyl)-5,8-diazaspiro[4.5]decane bromide;
3-(p-nitrophenyl)-3,6-diazaspiro[5.6]dodecane bromide;
8-phenyl-5,8-diazaspiro[4.5]decane bromide;
8-(p-methoxyphenyl)-5,8-diazaspiro[4.5]decane bromide;
8-(m-hydroxyphenyl)-5,8-diazaspiro[4.5]decane bromide;
8-(m-fluorophenyl)-5,8-diazaspiro[4.5]decane bromide;
8-(m-cyanophenyl)-5,8-diazaspiro[4.5]decane bromide;
8-(m-ethoxycarbonylphenyl)-5,8-diazaspiro[4.5]decane bromide;
8-(4-chloro-3-pyridyl)-5,8-diazaspiro[4.5]decane bromide;
8-(3-pyridyl)-5,8-diazaspiro[4.5]decane bromide;
8-(m-aminophenyl)-5,8-diazaspiro[4.5]decane bromide;
8-(m-methoxycarbonylphenyl)-5,8-diazaspiro[4.5]decane bromide;
2,4-dimethyl-9-allyl-3-oxo-6,9-diazaspiro[5.5]undecane chloride;
2,4-dimethyl-9-γ-phenylpropyl-3-oxo-6,9-diazaspiro[5.5]undecane chloride;
2,4-dimethyl-9-cinnamyl-3-oxo-6,9-diazaspiro[5.5]undecane chloride;
2,4-dimethyl-9-(2-pyridyl)-3-oxo-6,9-diazaspiro[5.5]undecane chloride.

8-(m-nitrophenyl)-7-methyl-5,8-diazaspiro[4.5]decane bromide; and 2,4,7-trimethyl-9-β-phenylethyl-3-oxo-6,9-diazaspiro[5.5]undecane chloride.

The another object of the present invention is to provide a process for preparing the compounds of die present invention. The compounds of the present invention can be prepared by the routine procedures in chemical field, preferably, the process for preparing the present compounds as follows:

Method One:
(1) in the presence of catalyst, compound (A) is reacted with compound (B) in solvent under 40~140° C. to produce compound (C), wherein the solvent is selected from a group consisting of alcohols, ketones, nitriles, chlorohydrocarbons, benzene series solvents, DMSO and DMF; the catalyst is inorganic bases or organic bases:

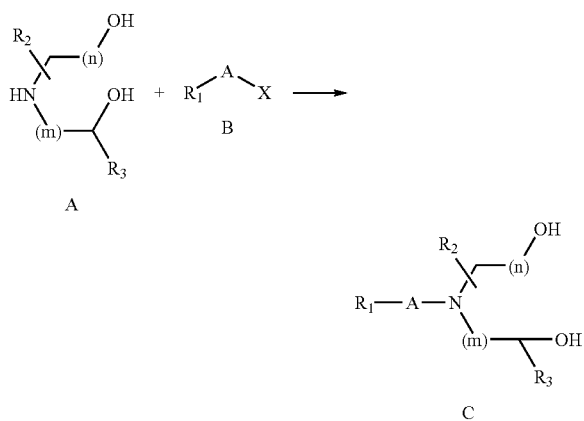

(2) chlorating the obtained product (C) at the temperature of 0~80° C. to give compound (D), wherein the solvent used in chloration is non-protonic solvents, and the chlorating reagent used is selected from the group consisting of thionyl chloride, phosphorus trichloride and phosphoric pentachloride:

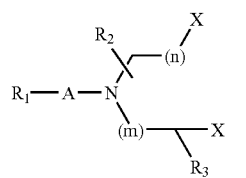

(3) in tire presence of catalyst, the compound (D) is reacted with compound (E) to produce the target compound (I) in a solvent under 40~140° C.:

wherein the solvent is selected from the group consisting of alcohols, ketones, nitriles, chlorohydrocarbons, benzene series solvents, DMSO and DMF; the catalyst is inorganic bases or organic bases.

In step (1) of Method One, the solvent used is selected from a group consisting of alcohols, ketones, nitriles, chlorohydrocarbons, benzene series solvents, DMSO and DMF. Wherein, the "alcohols" is for example methanol, ethanol, isopropanol and glycol, etc.; the "ketones" is for example acetone or methyl ethyl ketone, etc.; tire "nitriles" is for example acetonitrile, etc.; the "chlorohydrocarbons" is for example, chloroform or dichloromethane, etc.; the "benzene series solvents" is for example, benzene, toluene or xylene, etc. The solvent preferably is methanol, ethanol, isopropanol, acetonitrile, acetone, toluene, benzene, DMSO, DMF, chloroform or dichloromethane, more preferably ethanol.

In step (1) of Method One, the "catalyst" used is inorganic bases selected from oxides, hydroxides, carbonates, dicarbonates of alkali metals or alkaline-earth metals, etc., or organic bases selected from triethylamine or iso-propanolamine, etc. Preferably the base catalyst is sodium carbonate.

In Step (1) of Method One, the reaction temperature is preferably at 80° C.

In step (2) of Method One, the solvent used is non-protonic solvents, such as dichloromethane, chloroform, benzene or toluene etc., preferably chloroform; the chlorating reagent is preferably thionyl chloride; the reaction temperature is preferably at 50° C.

In step (3) of Method One, the solvent used is selected from a group consisting of alcohols, ketones, nitriles, chlorohydrocarbons, benzene series solvents, DMSO and DMF. Wherein, the "alcohols" is for example methanol, ethanol, isopropanol and glycol, etc.; the "ketones" is for example acetone or methyl ethyl ketone, etc.; the "nitriles" is for example acetonitrile, etc.; the "chlorohydrocarbons" is for example, chloroform or dichloromethane, etc.; the "benzene series solvents" is for example, benzene, toluene or xylene, etc. The solvent preferably is methanol, ethanol, isopropanol, acetonitrile, acetone, toluene, benzene, DMSO, DMF, chloroform, dichloromethane or glycol, more preferably ethanol.

In step (3) of Method One, the "catalyst" used is inorganic bases selected from oxides, hydroxides, carbonates, dicarbonates of alkali metals or alkaline-earth metals, etc., or organic base selected from triethylamine or iso-propanolamine, etc. Preferably, the base catalyst is sodium dicarbonate.

In step (3) of Method One, the reaction temperature is preferably at 80° C.

Method Two:
The present invention also provide the second method for preparing the compounds of the present invention. The method included the following steps:
(1) in the presence of catalyst, compound (F):

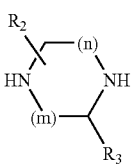

is reacted with compound (B) of $R_1$-A-X in solvent to produce intermediate compound (G), when $R_1$-A-X is non-aromatic halide, the reaction temperature is at 40~140° C., the solvent is selected from a group consisting of alcohols, ketones, nitriles, chloro-hydrocarbons, benzene series solvents, DMSO and DMF, and tire catalyst is various inorganic bases or organic bases; when $R_1$-A-X is aromatic halide, the reaction temperature is at −20~140° C., the solvent is protonic solvents, the catalyst is selected from a group consisting of cuprous iodide, cuprous chloride, cuprous bromide and cuprous oxide, an inorganic base is simultaneously added, the inorganic bases selected from a group consisting of potassium phosphate, potassium carbonate, sodium carbonate, sodium dicarbonate and sodium hydroxide:

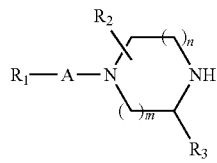

(2) in the presence of catalyst, the obtained compound (G) is reacted with compound (H):

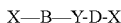—B—-D-X     H at the temperature of 40~140° C. in solvent to provide the target compound (I); wherein the solvent is selected from a group consisting of alcohols, ketones, nitriles, chlorohydrocarbons, benzene series solvents, DMSO and DMF; and tire catalyst used is inorganic bases or organic bases.

In step (1) of Method Two, when the starting material of Formula (B) is non-aromatic halide, the solvent used is selected from a group consisting of alcohols, ketones, nitriles, chlorohydrocarbons, benzene series solvents, DMSO and DMF. Wherein, the "alcohols" is for example methanol, ethanol, isopropanol and glycol, etc.; the "ketones" is for example acetone or methyl ethyl ketone, etc.; the "nitriles" is for example acetonitrile, etc.; the "chlorohydrocarbons" is for example, chloroform or dichloromethane, etc.; the "benzene series solvents" is for example, benzene, toluene or xylene, etc. The solvent preferably is methanol, ethanol, isopropanol, acetonitrile, acetone, toluene, benzene, DMSO, DMF, chloroform or dichloromethane, more preferably ethanol. The "catalyst" used is inorganic bases selected from oxides, hydroxides, carbonates, dicarbonates of alkali metals or alkaline-earth metals, etc., or organic bases selected from triethylamine or iso-propanolamine, etc. Preferably, the base catalyst is sodium carbonate. The reaction temperature is preferably at about 80° C.

In step (1) of Method Two, when the starting material of Formula (B) is aromatic halide, the solvent used is protonic solvent, preferably methanol, ethanol, propanol, isopropanol, glycol or glycerol, more preferably isopropanol. The catalyst is preferably cuprous iodide, and inorganic base simultaneously added is preferably potassium phosphate. The reaction temperature is preferably at about 20° C.

In step (2) of Method Two, the solvent used is selected from a group consisting of alcohols, ketones, nitriles, chlorohydrocarbons, benzene series solvents, DMSO and DMF, Wherein, the "alcohols" is for example methanol, ethanol, isopropanol and glycol, etc.; the "ketones" is for example acetone or methyl ethyl ketone, etc.; the "nitriles" is for example acetonitrile, etc.; tire "chlorohydrocarbons" is for example, chloroform or dichloromethane, etc.; the "benzene series solvents" is for example, benzene, toluene or xylene, etc. The solvent preferably is methanol, ethanol, isopropanol, acetonitrile, acetone, toluene, benzene, DMSO, DMF, chloroform, dichloromethane or glycol, more preferably ethanol.

In step (2) of Method Two, the "catalyst" used is inorganic bases selected from oxides, hydroxides, carbonates, dicarbonates of alkali metals or alkaline-earth metals, etc., or organic base selected from triethylamine or iso-propanolamine, etc. Preferably, the base catalyst is sodium dicarbonate.

In step (2) of Method Two, the reaction temperature is preferably at 80° C.

In Method One and Method Two, $R_1$, $R_2$, $R_3$, A, X, B, Y, D, n and m axe defined as set forth above.

Purification of the compounds provided by Method One and Method Two can be carried out by a routine procedure in chemical field, for example recrystallization. The solvent system for recrystallization is selected from ethyl acetate-ethanol, acetone-ethanol, ethyl acetate-methanol, acetone-methanol, acetone-water, methanol, ethanol or isopropanol etc., preferably ethyl acetate-ethanol.

Another object of the present invention is to provide an analgesic pharmaceutical composition comprising a compound represented by general formula (I) as active component, and optionally containing pharmaceutically acceptable carriers. If necessary, the content of active ingredients in the composition is in the range of 0.1-99%, and the remaining is pharmaceutically acceptable carriers.

The composition of the invention can be prepared by the routine methods in tire pharmaceutical field to provide various pharmaceutical preparations, such as oral preparations, injections, rectal administration preparations, local administration preparations, for example tablets, pills, dispersing powders, capsules, granules, emulsions, solutions, suspensions, syrups, solid suppository preparations for vaginal or rectal administration, patches for local application etc. Preferably, the preparation is injections, oral preparations or preparations for transdermal local administration, more preferably, the corresponding sustained and controlled release preparations.

The pharmaceutical composition and various preparations thereof are prepared by the routine methods in pharmaceutical field.

In order to prepare the suitable formulations, pharmaceutical carriers are added, if desired. The pharmaceutical carriers include various pharmaceutical auxiliary materials, such as excipients, fillers, diluents, disintegrants, surfactants, wetting agents, preservatives, flavoring agents, pigments, and so on.

The appropriate preparations and dose are determined according to the type of disease, severity and the status of the patients, such as gender, age, weight, and so on, usually 1-200 mg/kg (body weight)/day for the adults, preferably 1-50 mg/kg (body weight)/Day.

The third object of the invention is to provide the uses of the compounds represented by general formula (I), or their stereoisomers, tautomers, prodrugs, pharmaceutical acceptable salts in manufacturing analgesic drug, including the use of preparing the above substances into pharmaceutical preparations for practical application.

The fourth object of the invention is to provide a method for analgesic, which includes administering to a patient in need thereof a therapeutically effective amount of the compound represented by general formula (I), or their stereoisomers, tautomers, prodrugs and pharmaceutical acceptable salts.

The compound of general formula (1), or their stereoisomers, tautomers, prodrugs and pharmaceutical acceptable salts have a good analgesic activity and no any addiction. It will have a wide applications and exploitation in the future.

BEST MODE FOR CARRYING OUT THE INVENTION

Figure 1:
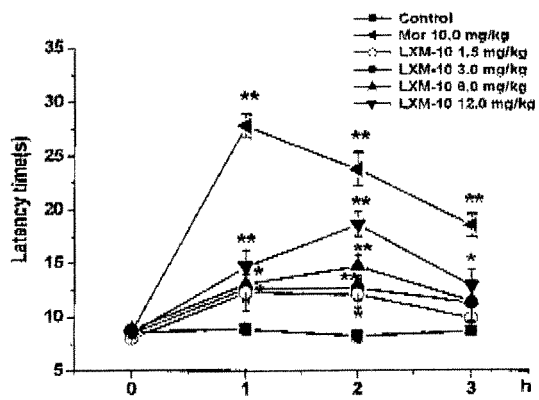
FIG. 1. Analgesic activity of LXM-10 (sc) in hot-plate test.

The following examples further illustrate the compounds of the invention, preparation methods and uses thereof without any way limiting its scope. The skilled in the art should be understood that any replacement or modification according to tire spirit of this invention is fallen into the scope of protection.

EXAMPLE 1

3-(β-phenylethyl)-3,6-diazaspiro[5.5]undecane chloride (LXM-1)

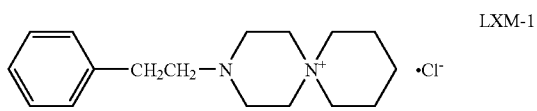

In 50 ml round-bottom flask, 25 ml ethanol was added, then 0.50 g N,N-bis(2-chloroethyl)phenylethylamine, 0.18 g hexahydropyridine were added then 1.50 g NaHCO$_3$ which is grinded were added under stirring. The reaction mixture was refluxed for 6 h at 80° C. until the reaction was completed. The reaction product was filtrated, and removing NaHCO$_3$, obtained crude product was concentrated. The product was recrystallized with ethanol/ethyl acetate to produce a white flaky crystal 0.56 g in 93.5% yield. Mp: 221-225° C. $^1$H-NMR (D$_2$O, 300 MHz): 7.10-7.23 (m, 5H, ArH), 3.27 (t, J=6.0 Hz, 8H, N$^+$—CH$_2$), 2.63-2.66 (m, 4H, N—CH$_2$), 2.74 (s, 4H, Ph-CH$_2$—CH$_2$), 1.67 (t, J=5.7 Hz, 4H, N$^+$—C—CH$_2$—C), 1.49 (t, J=6.0 Hz, 2H, N$^+$—C$_2$—CH$_2$—C$_2$). Anal. Calcd for C$_{17}$H$_{27}$ClN$_2$.H$_2$O: theoretical value: C, 65.26%; H, 9.34%; N, 8.95%; found: C, 65.60%; H, 9.28%; N, 8.70%.

EXAMPLE 2

3-methyl-9-(β-phenylethyl)-3,6,9-triazaspiro[5.5] undecane chloride (LXM-2)

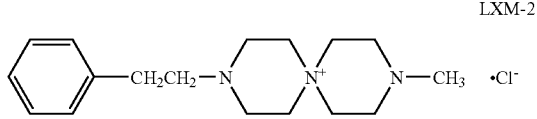

The compound LXM-2 was synthesized by using the method similar to the method described in Example 1. N,N-bis(2-chloroethyl)phenylethylamine and N-methyl piperazine were reacted. The crude product was recrystallized with ethanol/ethyl acetate to produce 0.54 g white cluster crystal in 85.8% yield. Mp: 194° C. (dec). $^1$H-NMR (D$_2$O, 300 MHz): 7.10-7.24 (m, 5H, ArH), 3.43 (bs, 8H, N$^+$—CH$_2$), 2.77 (bs, 4H, Ph-CH$_2$—CH$_2$), 2.61-2.68 (m, 8H, N$^+$—CH$_2$), 2.20 (s, 3H, CH$_3$). $^{13}$C-NMR (D$_2$O, 300 MHz): 140.12, 129.37, 129.31, 127.13, 58.67, 47.35, 45.68, 44.25, 32.45. Anal. Calcd for C$_{17}$H$_{28}$ClN$_3$.1.3H$_2$O: theoretical value: C, 61.26%; H, 9.25%; N, 12.61%; found: C, 61.32%; H, 9.11%; N, 12.52%.

EXAMPLE 3

3-(β-phenylethyl)-3,6-diazaspiro[5.5]-benzo[8,9] undecane chloride (LXM-3)

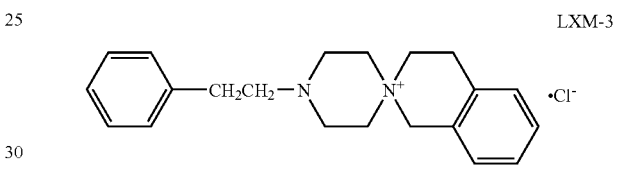

The compound LXM-3 was synthesized by using the method similar to the method described in Example 1. N,N-bis(2-chloroethyl)phenylethylamine and tetrahydroisoquinoline were reacted. The crude product was recrystallized with ethanol/ethyl acetate to produce 0.57 g white powder in 81.9% yield. Mp: 202-204° C. $^1$H-NMR (D$_2$O, 300 MHz): 7.03-7.24 (m, 9H, ArH), 4.50 (s, 2H, Ph-CH$_2$—N$^+$), 3.65 (t, J=6.3 Hz, 2H, N$^+$—CH$_2$—C-Ph), 3.35 (t, J=4.8 Hz 4H, N$^+$—CH$_2$), 3.05 (t, J=6.6 Hz, 2H, N$^+$—C—CH$_2$-Ph), 2.82 (s, 4H, N—CH$_2$), 2.63-2.66 (m, 4H, Ph-CH$_2$—CH$_2$). Anal. Calcd for C$_{21}$H$_{27}$ClN$_2$.1.9H$_2$O: theoretical value: C, 66.88%; H, 8.23%; N, 7.43%; found: C, 67.00%; H, 7.64%; N, 7.30%.

EXAMPLE 4

3-methyl-9-benzyl-3,6,9-triazaspiro[5.5]undecane chloride (LXM-4)

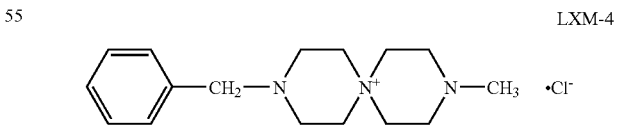

The compound LXM-4 was synthesized by using the method similar to the method described in Example 1. N,N-bis(2-chloroethyl)benzylamine and N-methyl piperazine were reacted. The crude product was recrystallized with ethanol/ethyl acetate to produce 0.15 g white powder in 51.6% yield. Mp: 180° C. (dec). $^1$H-NMR (D$_2$O, 300 MHz): 7.18-

7.28 (m, 5H, ArH), 3.53 (s, 2H, PhCH$_2$), 3.39 (bs, 8H, N—CH$_2$), 2.65-2.70 (m, 8H, N$^+$—CH$_2$), 2.17 (s, 3H, CH$_3$).

EXAMPLE 5

2,4-dimethyl-9-β-(p-nitrophenyl)ethyl-3-oxo-6,9-diazaspiro[5.5]undecane chloride (LXM-5)

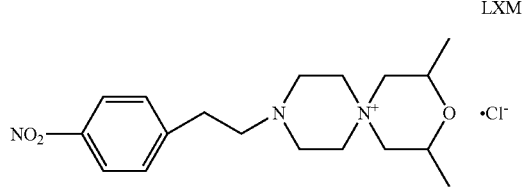

LXM-5

The compound LXM-5 was synthesized by using the method similar to the method described in Example 1. N,N-bis(2-chloroethyl)-p-nitrophenylethylamine and 2,6-dimethylmorpholine were reacted. The crude product was recrystallized with ethanol/ethyl acetate to produce 0.44 g buff powder crystal. Mp: 288-294° C. $^1$H-NMR (D$_2$O, 300 MHz): 8.01 (d, J=8.4 Hz, 2H, ArH), 7.30 (d, 2H, J=8.4 Hz, ArH), 4.05-4.11 (m, 2H, O—CH), 3.59-3.62 (m, 4H, N$^+$—CH$_2$), 3.35 (t, J=4.8 Hz, 2H, Ar—CH$_2$), 2.64-2.94 (m, 10H, N$^+$—CH$_2$, N—CH$_2$), 1.07 (d, J=6.3 Hz, 6H, CH$_3$). Anal. Calcd for C$_{18}$H$_{28}$ClN$_3$O$_3$: theoretical value: C, 58.45%; H, 7.63%; N, 11.36%; found: C, 58.75%; H, 7.67%; N, 11.31%.

EXAMPLE 6

3-methyl-9-(β-phenylethyl)-6,9-diazaspiro[5.5]undecane chloride (LXM-6)

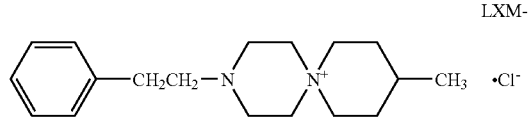

LXM-6

The compound LXM-6 was synthesized by using the method similar to the method described in Example 1. N,N-bis(2-chloroethyl)phenylethylamine and 4-methyl hexahydropyridine were reacted. The crude product was recrystallized with ethanol/ethyl acetate to produce 0.53 g white powder in 84.5% yield. Mp: 230° C. (dec). $^1$H-NMR (D$_2$O, 300 MHz): 7.09-7.23 (m, 5H, ArH), 3.02-3.53 (m, 8H, N$^+$—CH$_2$), 2.76-2.78 (m, 4H, N—CH$_2$) 2.57-2.70 (m, 4H, Ph-CH$_2$—CH$_2$), 1.60-1.69 (m, 2H, CH$_2$—C—CH$_3$), 1.58 (m, 1H, CH), 1.40-1.49 (m, 2H, CH$_2$—C—CH$_3$), 0.81 (d, J=6.3 Hz, 3H, CH$_3$). Anal. Calcd for C$_{18}$H$_{29}$ClN$_2$.H$_2$O: theoretical value: C, 66.13%; H, 9.56%; N, 8.57%; found: C, 66.12%; H, 9.40%; N, 8.58%.

EXAMPLE 7

2,4-dimethyl-9-β-(p-methoxyphenyl)ethyl-3-oxo-6,9-diazaspiro[5.5]undecane chloride (LXM-7)

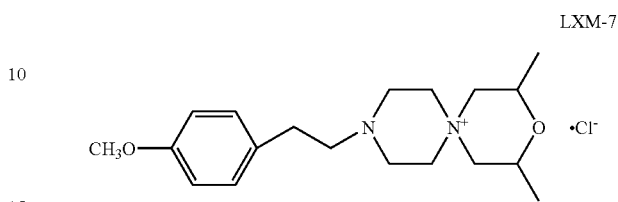

LXM-7

The compound LXM-7 was synthesized by using the method similar to the method described in Example 1. N,N-bis(2-chloroethyl)-p-methoxyphenylethylamine and 2,6-dimethylmorpholine were reacted. The crude product was recrystallized with ethanol/ethyl acetate to obtain the desired product. MS-FAB (M+1): 355.21. Anal. Calcd for C$_{19}$H$_{31}$ClN$_2$O$_2$.0.5H$_2$O: theoretical value: C, 62.71%; H, 8.86%; N, 7.70%; found: C, 62.68%; H, 8.98%; N, 7.38%.

EXAMPLE 8

2,4-dimethyl-9-β-(m-fluorophenyl)ethyl-3-oxo-6,9-diazaspiro[5.5]undecane chloride (LXM-8)

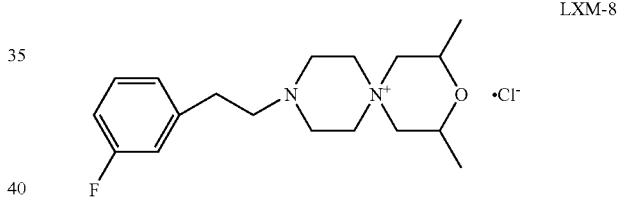

LXM-8

The compound LXM-8 was synthesized by using the method similar to the method described in Example 1. N,N-bis(2-chloroethyl)-m-fluorophenylethylamine and 2,6-dimethylmorpholine were reacted. The crude product was recrystallized with ethanol/ethyl acetate to obtain the desired product. MS-FAB (M+1): 343.19. Anal. Calcd for C$_{18}$H$_{28}$ClFN$_2$O: theoretical value: C, 63.05%; H, 8.23%; N, 8.17%; found: C, 63.10%; H, 8.12%; N, 8.05%.

EXAMPLE 9

2,4-dimethyl-9-β-(m-nitrophenyl)ethyl-3-thio-6,9-diazaspiro[5.5]undecane chloride (LXM-9)

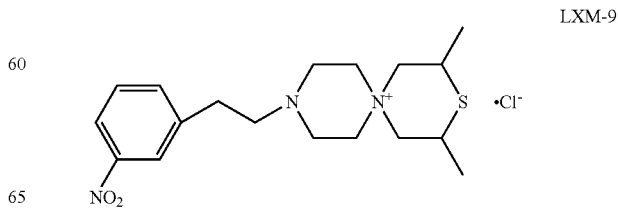

LXM-9

The compound LXM-9 was synthesized by using the method similar to the method described in Example 1. N,N-bis(2-chloroethyl)-m-nitrophenylethylamine and 2,6-dimethyl-thiomorpholine were reacted. The crude product was recrystallized with ethanol/ethyl acetate to obtain the desired product. MS-FAB (M+1): 387.16. Anal. Calcd for $C_{18}H_{28}ClN_3O_2S$: theoretical value: C, 56.02%; H, 7.31%; N, 10.89%; found: C, 56.20%; H, 7.12%; N, 11.05%.

EXAMPLE 10

2,4-dimethyl-9-β-phenylethyl-3-oxo-6,9-diazaspiro[5.5]undecane chloride (LXM-10)

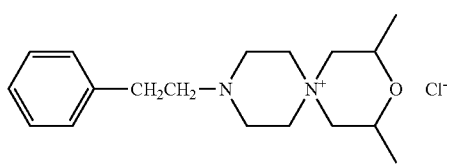

The compound LXM-10 was synthesized by using the method similar to the method described in Example 1. N,N-bis(2-chloroethyl)-phenylethylamine and 2,6-dimethylmorpholine were reacted. The crude product was recrystallized with ethanol/ethyl acetate to obtain 0.83 g white powder in 83.8% yield. Mp: 220° C. (dec). $^1$H-NMR (D$_2$O, 300 MHz): 7.12-7.26 (m, 5H, ArH), 4.05-4.14 (m, 2H, CH), 3.30-3.64 (m, 8H, N$^+$—CH$_2$), 2.79-2.95 (m, 4H, N—CH$_2$), 2.61-2.74 (m, 4H, Ph-CH$_2$—CH$_2$), 1.05 (d, J=11.7 Hz, 6H, CH$_3$). Anal. Calcd for $C_{18}H_{29}ClN_2O \cdot 1.1H_2O$: theoretical value: C, 62.72%; H, 9.12%; N, 8.13%; found: C, 62.50%; H, 9.12%; N, 8.05%.

EXAMPLE 11

8-(4-chloro-2,3-pyridazinyl)-5,8-diazaspiro[4.5]decane chloride (LXM-11)

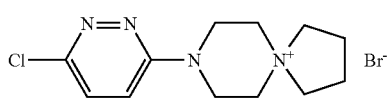

The compound LXM-11 was synthesized by using the method similar to the method described in Example 15. 3,6-dichloropyridazine is reacted with piperazine to give the intermediate, and then the intermediate and 1,4-dibromobutane were reacted. The crude product was recrystallized with ethanol/ethyl acetate to obtain 1.60 g white powder in 95.6% yield. Mp: 220° C. $^1$H-NMR (D$_2$O, 300 MHz): 7.40 (d, J=9.3 Hz, 1H, ArH), 7.24 (d, J=9.3 Hz, 1H, ArH), 3.79 (bs, 4H, N—CH$_2$), 3.51 (t, J=7.2 Hz, N$^+$—CH$_2$), 3.45 (t, J=5.1 Hz, N$^+$—CH$_2$), 2.08 (bs, 4H, C—CH$_2$—CH$_2$—C).

EXAMPLE 12

8-(β-phenylethyl)-5,8-diazaspiro[4.5]decane chloride (LXM-12)

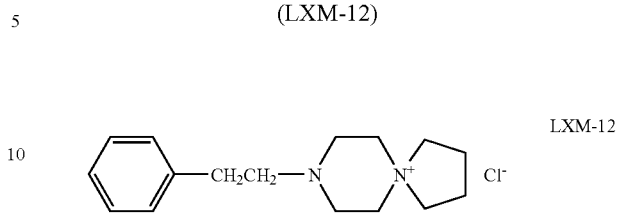

The compound LXM-12 was synthesized by using the method similar to the method described in Example 1. N,N-bis(2-chloroethyl)-phenylethylamine and tetrahydropyrrole were reacted. The crude product was recrystallized with ethanol/ethyl acetate to obtain 0.71 g white powder in 83.1% yield. Mp: 220° C. (dec). $^1$H-NMR (D$_2$O, 300 MHz): 7.11-7.25 (m, 5H, ArH), 3.30 (t, J=7.8 Hz, N$^+$—CH$_2$), 3.41 (t, J=5.1 Hz, N$^+$—CH$_2$), 2.77 (bs, 4H, N—CH$_2$), 2.58-2.73 (m, 4H, Ph-CH$_2$—CH$_2$), 2.03-2.05 (m, 4H, C—CH$_2$—CH$_2$—C).

EXAMPLE 13

3-(β-phenylethyl)-3,6-diazaspiro[5.6]dodecane chloride (LXM-13)

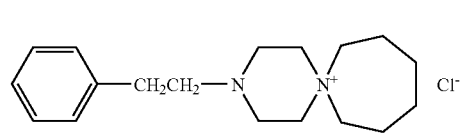

The compound LXM-13 was synthesized by using the method similar to the method described in Example 1. N,N-bis(2-chloroethyl)-phenylethylamine and aza-cycloheptane were reacted. The crude product was recrystallized with ethanol/ethyl acetate to obtain 0.79 g white powder in 84.0% yield. Mp: 220° C. (dec). $^1$H-NMR (D$_2$O, 300 MHz): 7.10-7.24 (m, 5H, ArH), 3.31 (t, J=4.5 Hz, 8H, N$^+$—CH$_2$), 2.76 (bs, 4H, N—CH$_2$), 2.64-2.67 (m, 4H, Ph-CH$_2$—(CH$_2$), 1.73 (bs, 4H, N$^+$—C—CH$_2$—C), 1.53 (bs, 4H, N$^+$—C—C—CH$_2$). Anal. Calcd for $C_{18}H_{29}ClN_2 \cdot 0.5H_2O$: theoretical value: C, 68.01%; H, 9.51%; N, 8.81%; found: C, 67.97%; H, 9.70%; N, 8.73%.

EXAMPLE 14

9-β-phenylethyl-3-oxo-6,9-diazaspiro[5.5]undecane chloride (LXM-14)

The compound LXM-14 was synthesized by using the method similar to the method described in Example 1. N,N-bis(2-chloroethyl)-phenylethylamine and morpholine were reacted. The crude product was recrystallized with ethanol/ethyl acetate to obtain 0.75 g white powder in 83.1% yield. Mp: 220° C. (dec). $^1$H-NMR (D$_2$O, 300 MHz): 7.11-7.25 (m, 5H, ArH), 3.86 (t, J=5.1 Hz, 4H, O—CH$_2$), 3.48-3.49 (m, 8H, N$^+$—CH$_2$), 2.80 (bs, 4H, N—CH$_2$), 2.60-2.72 (m, 4H, Ph-CH$_2$—CH$_2$). Anal. Calcd for C$_{16}$H$_{25}$ClN$_2$O.0.5H$_2$O: theoretical value: C, 62.83%; H, 8.57%; N, 9.16%; found: C, 62.89%; H, 8.51%; N, 9.18%.

EXAMPLE 15

8-(p-nitrophenyl)-5,8-diazaspiro[4.5]decane bromide (LXM-15)

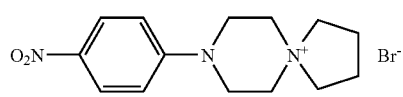

LXM-15

8.10 g p-nitro-bromobenzene was added into a 250 ml round-bottom flask containing 50 mL isopropanol, then 7.00 g anhydrous piperazine, 15.00 g anhydrous K$_3$PO$_4$ and 4 ml glycol was added, then 2.00 g CuI was added as catalyster under nitrogen atmosphere (the small-scale reaction was carried out in the absence of nitrogen atmosphere, the results showed mat the yield was low probably because of the oxidation of CuI). The reaction mixture was refluxed for two days under nitrogen atmosphere. The crude product was filtered and concentrated. The concentrate was extracted with chloroform/water. The chloroform extract was dried by anhydrous Na$_2$SO$_4$. Based on higher polarity of product and lower polarity of the starting material, the extract was purified by column-chromatography with gradient elution of petroleum ether:ethyl acetate:ethanol in differ ratio, concentrated the eluate, to produce N-4-nitro-phenyl piperazine as yellow solid (4.10 g, 49.4% yield). Mp: 126-128° C. (lit.: 130-132° C.)

0.81 g N-4-nitrophenyl piperazine and 0.88 g 1,4-dibromobutane were added into a 50 ml round-bottom flask containing 25 mL ethanol, 3.00 g anhydrous NaHCO$_3$ was grinded and added with stirring. The reaction mixture was refluxed for 6 h at 80° C. until die reaction was completed. The crude product was filtered, removed NaHCO$_3$ and concentrated. The filtrate is washed with ethyl acetate to obtain the crude product 1.14 g in 85.2% yield. The product was recrystallized with ethanol/ethyl acetate to produce white powder. Mp: 278-280° C. $^1$H-NMR (D$_2$O, 300 MHz): 8.00 (d, J=9.6 Hz, 2H, ArH), 6.90 (d, 2H, J=9.6 Hz, ArH), 3.67 (bs, 4H, Ph-N—CH$_2$), 3.48-3.57 (m, 8H, N$^+$—CH$_2$), 2.11 (bs, 4H, N$^+$—C—CH$_2$—CH$_2$—C—N$^+$). Anal. Calcd for C$_{14}$H$_{20}$BrN$_3$O$_2$.0.1H$_2$O: theoretical value: C, 48.88%; H, 5.92%; N, 12.21%; found: C, 48.73%; H, 6.28%; N, 11.94%.

EXAMPLE 16

8-(m-nitrophenyl)-5,8-diazaspiro[4.5]decane bromide (LXM-16)

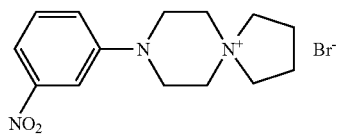

LXM-16

The compound LXM-16 was synthesized by using the method similar to the method described in Example 15. m-nitro-iodobenzene was reacted with piperazine to give the intermediate, and then the intermediate and 1,4-dibromobutane were reacted. The crude product was recrystallized with ethanol/ethyl acetate to obtain 0.80 g yellow powder crystal in 96.6% yield. Mp: 246-249° C. $^1$H-NMR (D$_2$O, 300 MHz): 7.72 (s, 1H, ArH), 7.65 (d, J=8.1 Hz, 1H, ArH), 7.36 (t, J=8.1 Hz, 1H, ArH), 7.28 (d, J=9.0 Hz, 1H, ArH), 3.50-3.54 (m, 12H, N$^+$—CH$_2$, N—CH$_2$),), 2.08 (bs, 4H, C—CH$_2$—CH$_2$—C). Anal. Calcd for C$_{14}$H$_{20}$Cl$_2$N$_3$.0.2H$_2$O: theoretical value: C, 48.62%; H, 5.95%; N, 12.15%; found: C, 48.42%; H, 5.74%; N, 11.99%.

EXAMPLE 17

3-(p-nitrophenyl)-3,6-diazaspiro[5.6]dodecane bromide (LXM-17)

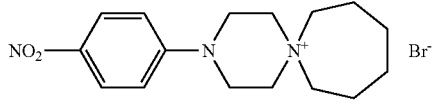

LXM-17

The compound LXM-17 was synthesized by using the method similar to the method described in Example 15. p-nitro-iodobenzene was reacted with piperazine to give the intermediate, and then the intermediate and 1,6-dibromohexane were reacted. The crude product was obtained in 45% yield. The crude product was recrystallized with ethanol/ethyl acetate to obtain yellow flaky crystal. Mp: 255-257° C. $^1$H-NMR (D$_2$O, 300 MHz): 8.03 (d, J=9.0 Hz, 2H, ArH), 6.90 (d, 2H, J=9.0 Hz, ArH), 3.66 (bs, 4H, Ph-N—CH$_2$), 3.47-3.54 (m, 8H, N$^+$—CH$_2$), 1.81 (bs, 4H, N$^+$—C—CH$_2$—C—CH$_2$—C—N$^+$), 1.59 (bs, 4H, N$^+$—C—C—CH$_2$—CH$_2$—C—C—N$^+$) Anal. Calcd for C$_{16}$H$_{24}$BrN$_3$O$_2$.H$_2$O: theoretical value: C, 51.90%; H, 6.53%; N, 11.35%; found: C, 51.87%; H, 6.68%; N, 11.00%.

EXAMPLE 18

8-phenyl-5,8-diazaspiro[4.5]decane bromide (LXM-18)

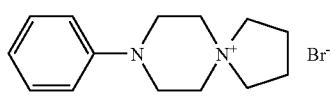

LXM-18

The compound LXM-18 was synthesized by using the method similar to the method described in Example 15. Iodobenzene was reacted with piperazine to give the intermediate, and then the intermediate and 1,4-dibromobutane were reacted. 1.28 g crude product was obtained in 93.1% yield. The crude product was recrystallized with ethanol/ethyl acetate to obtain white powder. Mp: 208-209° C. $^1$H-NMR (D$_2$O, 300 MHz): 7.25 (dd, J=7.2 Hz, 8.7 Hz, 2H, ArH), 7.OO (d, J=8.4 Hz, 1H, ArH), 6.92 (t, J=7.5 Hz, 2H, ArH), 3.46-3.54 (m, 8H, N$^+$—CH$_2$), 3.39 (t, J=4.5 Hz, 4H, N—CH$_2$), 2.01 (bs, 4H, N$^+$—C—CH$_2$). Anal. Calcd for C$_{14}$H$_{21}$BrN$_2$.0.3H$_2$O: theoretical value: C, 55.56%; H, 7.19%; N, 9.26%; found: C, 55.55%; H, 6.91%; N, 9.26%.

EXAMPLE 19

8-(p-methoxyphenyl)-5,8-diazaspiro[4.5]decane bromide (LXM-19)

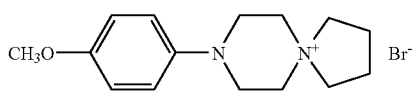

LXM-19

The compound LXM-19 was synthesized by using the method similar to the method described in Example 15. p-methoxy-iodobenzene was reacted with piperazine to give the intermediate, and then the intermediate and 1,4-dibromobutane were reacted. 1.03 g crude product was obtained in 89.8% yield. The crude product was recrystallized with ethanol/ethyl acetate to obtain salmon pink flaky crystal. Mp: 201-203° C. $^1$H-NMR (D$_2$O, 300 MHz): 6.93-6.99 (m, 2H, O—C—CH), 6.84-6.88 (m, 2H, O—C$_2$—CH), 3.65 (s, 3H, CH$_3$), 3.44-3.52 (m, 8H, N$^+$—CH$_2$), 3.28 (bs, 4H, N—CH$_2$), 2.07 (bs, 4H, N$^+$—C—CH$_2$). Anal. Calcd for C$_{15}$H$_{23}$BrN$_2$O: theoretical value: C, 55.05%; H, 7.08%; N, 8.56%; found: C, 55.00%; H, 7.07%; N, 8.55%.

EXAMPLE 20

8-(m-hydroxyphenyl)-5,8-diazaspiro[4.5]decane bromide (LXM-20)

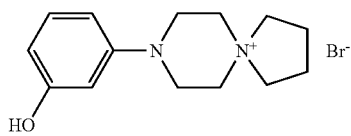

LXM-20

The compound LXM-20 was synthesized by using the method similar to the method described in Example 15. m-hydroxy-iodobenzene was reacted with piperazine to give the intermediate, and then the intermediate and 1,4-dibromobutane were reacted. The crude product was recrystallized with ethanol/ethyl acetate to obtain the desired product. MS-FAB (M+1): 314.08. Anal, Calcd for C$_{14}$H$_{21}$BrN$_2$O: theoretical value: C, 53.68%; H, 6.76%; N, 8.94%; found: C, 53.80%; H, 6.87%; N, 8.75%.

EXAMPLE 21

8-(m-fluorophenyl)-5,8-diazaspiro[4.5]decane bromide (LXM-21)

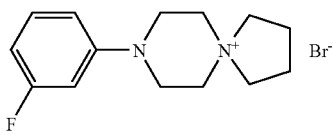

LXM-21

The compound LXM-21 was synthesized by using the method similar to the method described in Example 15. m-fluoroiodobenzene was reacted with piperazine to give the intermediate, and then the intermediate and 1,4-dibromobutane were reacted. The crude product was recrystallized with ethanol/ethyl acetate to obtain the desired product. MS-FAB (M+1): 316.08. Anal. Calcd for C$_{14}$H$_{20}$FN$_2$: theoretical value: C, 53.34%; H, 6.40%; N, 8.89%; found: C, 53.40%; H, 6.17%; N, 8.75%.

EXAMPLE 22

8-(m-cyanophenyl)-5,8-diazaspiro[4.5]decane bromide (LXM-22)

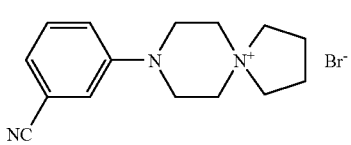

LXM-22

The compound LXM-22 was synthesized by using the method similar to the method described in Example 15. m-cyano-iodobenzene was reacted with piperazine to give the intermediate, and then the intermediate and 1,4-dibromobutane were reacted. The crude product was recrystallized with ethanol/ethyl acetate to obtain the desired product. MS-FAB (M+1): 323.08. Anal. Calcd for C$_{15}$H$_{20}$BrN$_3$: theoretical value: C, 55.91%; H, 6.26%; N, 13.04%; found: C, 56.00%; H, 6.47%; N, 13.15%.

EXAMPLE 23

8-(m-ethoxycarbonylphenyl)-5,8-diazaspiro[4.5]decane bromide (LXM-23)

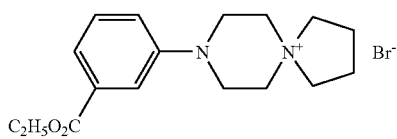

LXM-23

The compound LXM-23 was synthesized by using the method similar to the method described in Example 15. m-ethoxycarbonyl-iodobenzene was reacted with piperazine to give the intermediate, and then the intermediate and 1,4-dibromobutane were reacted. The crude product was recrystallized with ethanol/ethyl acetate to obtain the desired product, MS-FAB (M+1): 370.11. Anal. Calcd for $C_{17}H_{25}BrN_2O_2$: theoretical value: C, 55.29%; H, 6.82%; N, 7.59%; found: C, 55.40%; H, 7.07%; N, 7.55%.

EXAMPLE 24

8-(4-chloro-3-pyridyl)-5,8-diazaspiro[4.5]decane bromide (LXM-24)

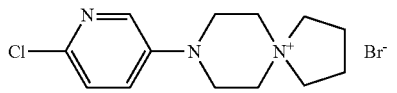

LXM-24

The compound LXM-24 was synthesized by using the method similar to the method described in Example 15. 2-chloro-5-iodopyridine was reacted with piperazine to give the intermediate, and then the intermediate and 1,4-dibromobutane were reacted. The crude product was recrystallized with ethanol/ethyl acetate to obtain the desired product. MS-FAB (M+1): 333.04. Anal. Calcd for $C_{13}H_{19}BrClN_3$: theoretical value: C, 46.94%; H, 5.76%; N, 12.63%; found: C, 47.00%; H, 5.67%; N, 12.55%.

EXAMPLE 25

8-(3-pyridyl)-5,8-diazaspiro[4.5]decane bromide (LXM-25)

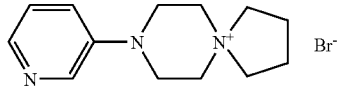

LXM-25

The compound LXM-25 was synthesized by using the method similar to the method described in Example 15. 3-iodopyridine was reacted with piperazine to give the intermediate, and then the intermediate and 1,4-dibromobutane were reacted. The crude product was recrystallized with ethanol/ethyl acetate to obtain the desired product. MS-FAB (M+1): 299.08. Anal. Calcd for $C_{13}H_{20}BrN_3$: theoretical value: C, 52.36%; H, 6.76%; N, 14.09%; found: C, 52.40%; H, 6.87%; N, 14.05%.

EXAMPLE 26

8-(m-aminophenyl)-5,8-diazaspiro[4.5]decane bromide (LXM-26)

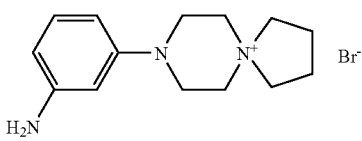

LXM-26

The compound LXM-26 was synthesized by using the method similar to the method described in Example 15. m-amino-iodobenzene was reacted with piperazine to give the intermediate, and then the intermediate and 1,4-dibromobutane were reacted. The crude product was recrystallized with ethanol/ethyl acetate to obtain the desired product. MS-FAB (M+1): 313.10. Anal. Calcd for $C_{14}H_{22}BrN_3$; theoretical value: C, 53.85%; H, 7.10%; N, 13.46%; found: C, 54.00%; H, 7.07%; N, 13.55%.

EXAMPLE 27

8-(m-methoxycarbonylphenyl)-5,8-diazaspiro[4.5]decane bromide (LXM-27)

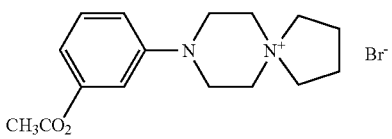

LXM-27

The compound LXM-27 was synthesized by using the method similar to the method described in Example 15. m-acetoxy-iodobenzene was reacted with piperazine to give the intermediate, and then the intermediate and 1,4-dibromobutane were reacted. The crude product was recrystallized with ethanol/ethyl acetate to obtain the desired product. MS-FAB (M+1): 356.09. Anal. Calcd for $C_{16}H_{23}BrN_2O_2$: theoretical value: C, 54.09%; H, 6.53%; N, 7.89%; found: C, 54.00%; H, 6.57%; N, 7.65%.

EXAMPLE 28

2,4-dimethyl-9-allyl-3-oxo-6,9-diazaspiro[5.5]undecane chloride (LXM-28)

LXM-28

The compound was synthesized by using the method similar to the method described in Example 1. N,N-bis(2-chloroethyl)allylamine and 2,6-dimethylmorpholine were reacted. The crude product was recrystallized with ethanol/ethyl acetate to obtain 1.34 g white powder in 43.8% yield. Mp: 236° C. (dec). $^1$H-NMR (D$_2$O, 300 MHz): 5.60-5.72 (m, 1H, =C<u>H</u>—), 5.12-5.18 (m, 2H, =C<u>H$_2$</u>), 4.05-4.10 (m, 2H, O—C<u>H</u>—CH$_3$), 3.58-3.64 (m, 4H, N$^+$—C<u>H$_2$</u>), 3.34 (t, 2H, =C—C<u>H$_2$</u>), 2.74-3.01 (m, 8H, N—C<u>H$_2$</u>, N$^+$—C<u>H$_2$</u>), 1.08 (d, J=12.0 Hz, 6H, C<u>H$_3$</u>). Anal. Calcd for C$_{13}$H$_{25}$ClN$_2$O: theoretical value: C, 59.87%; H, 9.66%; N, 10.74%; found: C, 59.62%; H, 9.61%; N, 10.60%.

EXAMPLE 29

2,4-dimethyl-9-γ-phenylpropyl-3-oxo-6,9-diazaspiro [5.5] undecane chloride (LXM-29)

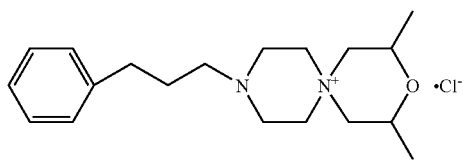

LXM-29

Similar as described in Example 1, the compound was synthesized from reagents N, N-bis(2-chloroethyl-phenyl-propylamine and 2,6-dimethylmorphine, correspondingly. Recrystallization of the crude product with ethanol/ethyl acetate produced 0.20 g white powder in 38% yield. Mp: 220° C. (dec). $^1$H-NMR (D$_2$O 300 MHz): 7.09-7.24 (m, 5H, ArH), 4.04-4.10 (m, 2H, O—C<u>H</u>—CH$_3$), 3.56-3.64 (m, 4H, N$^+$—C<u>H$_2$</u>), 3.33 (t, J=4.8 Hz, 2H, Ph-C<u>H$_2$</u>), 2.84 (t, J=12.0 Hz, 2H, Ph-C—C—C<u>H$_2$</u>), 2.71 (bs, 4H, N—C<u>H$_2$</u>), 2.84 (t, J=7.5 Hz, 2H, N—C<u>H$_2$</u>), 2.37 (t, J=7.5 Hz, 2H, N—C<u>H$_2$</u>), 1.64 (p, J=7.8 Hz, 2H, Ph-C—C<u>H$_2$</u>), 1.05 (d, J=11.7 Hz, 6H, C<u>H$_3$</u>). Anal. Calcd for C$_{19}$H$_{31}$ClN$_2$O: theoretical value: C, 67.33%; H, 9.22%; N, 8.27%; found: C, 67.29%; H, 9.12%; N, 8.11%.

EXAMPLE 30

2,4-dimethyl-9-cinnamenyl-3-oxo-6,9-diazaspiro [5.5] undecane chloride (LXM-30)

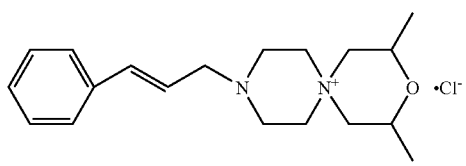

LXM-30

Similar as described in Example 1, compound LXM-30 was synthesized from reagents N,N-bis(2-chloroethyl)cinnamenylamine and 2,6-dimethylmorphine, correspondingly. Recrystallization of the crude product with ethanol/ethyl acetate produced 0.59 g white powder. Mp: 266-268° C. $^1$H-NMR (D$_2$O, 300 MHz): 7.15-7.35 (m, 5H, ArH), 6.51 (d, J=15.9 Hz, 1H, Ph-C<u>H</u>=), 6.06-6.16 (m, 1H, Ph-C=C<u>H</u>), 4.03-4.08 (m, 2H, O—C<u>H</u>), 2.77-3.58 (m, 14H, N$^+$—C<u>H$_2$</u>, N—C<u>H$_2$</u>), 1.06 (d, J=6.0 Hz, 6H, C<u>H$_3$</u>). Anal. Calcd for C$_{19}$H$_{29}$ClN$_2$O.0.4H$_2$O: theoretical value: C, 66.32%; H, 8.73%; N, 8.14%; found: C, 66.57%; H, 8.90%; N, 7.70%.

EXAMPLE 31

2,4-dimethyl-9-(2-pyridyl)-3-oxo-6,9-diazaspiro [5.5]undecane chloride (LXM-31)

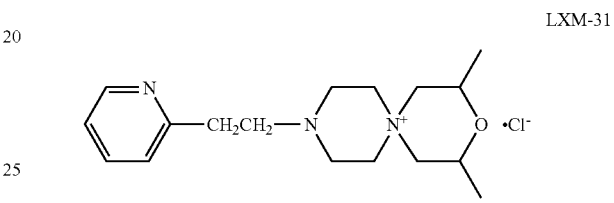

LXM-31

The compound LXM-31 was synthesized by using the method similar to the method described in Example 1. N,N-bis(2-chloroethyl)-2-pyridinylethamine and 2,6-dimethylmorpholine were reacted. The crude product was recrystallized with ethanol/ethyl acetate to obtain 0.31 g pink powder. Mp: 247° C. $^1$H-NMR (D$_2$O, 300 MHz): 8.26 (d, J=4.8 Hz, 1H, Ar<u>H</u>), 7.62 (t, J=7.8 Hz, 1H, Ar<u>H</u>), 7.20 (d, J=4.8 Hz, 1H, Ar<u>H</u>), 7.13 (t, J=6.6 Hz, 1H, Ar<u>H</u>), 4.05-4.11 (m, 2H, O—C<u>H</u>), 3.49-3.62 (m, 4H, N$^+$—C<u>H$_2$</u>), 3.34 (t, J=5.1 Hz, 2H, Ar—C<u>H$_2$</u>), 2.71-2.93 (m, 10H, N$^+$—C<u>H$_2$</u>, N—C<u>H$_2$</u>), 1.06 (d, J=6.0 Hz, 6H, C<u>H$_3$</u>). Anal. Calcd for C$_{17}$H$_{28}$ClN$_3$O, theoretical value: C, 62.66%; H, 8.66%; N, 12.89%; found: C, 62.38%; H, 8.63%; N, 12.68%.

EXAMPLE 32

8-(m-nitrophenyl)-7-methyl-5,8-diazaspiro[4.5]decane bromide (LXM-32)

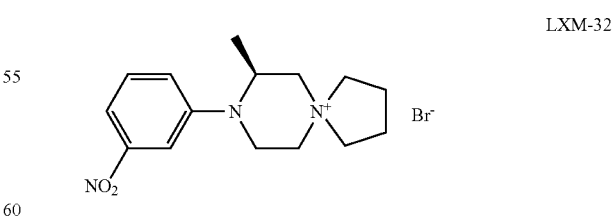

LXM-32

The compound LXM-32 was synthesized by using the method similar to the method described in Example 15. 3-iodo-nitrobenzene was reacted with 2-methyl-piperazine to give the intermediate, and then the intermediate and 1,4-dibromobutane were reacted. The crude product was recrystallized with ethanol/ethyl acetate to obtain the desired product. MS-FAB (M+1): 357.3. Anal. Calcd for $C_{15}H_{22}BrN_3O_2$: C, 50.57%; H, 6.22%; N, 11.79%; found: C, 50.40%; H, 6.37%; N, 12.05%.

EXAMPLE 33

2,4,7-trimethyl-9-β-phenylethyl-3-oxo-6,9-diazaspiro[5.5] undecane chloride (LXM-33)

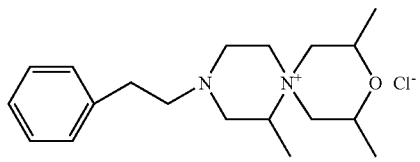

The compound LXM-33 was synthesized by using the method similar to the method described in Example 10. MS-FAB (M+1): 340.1. Anal. Calcd for $C_{19}H_{31}ClN_2O$: theoretical value: C, 67.33%; H, 9.22%; N, 8.27%; found: C, 67.40%; H, 9.37%; N, 8.05%.

EXAMPLE 34

Preparation of Capsules

Grinding 10 mg of compound LXM-10 into powders and encasing them into the hard capsules produced capsules.

EXAMPLE 35

Preparation of Capsules

Prescription of each capsule:

| | |
|---|---|
| LXM-10 | 10 mg |
| Lactose | 65 mg |
| Pregelatinzed starch | 25 mg |
| Cross-linked carboxymethylcellulose sodium | 3 mg |
| Magnesium stearate | 0.30 mg |

Sieving compound LXM-10, lactose, pregelatinized starch, cross-linked carboxymethylcellulose sodium, respectively, with boults of 65 mesh standard, and put them in store. Materials mentioned above were mixed uniformly with other auxiliary materials according to rank-increase by degree method and sieved with boults of 65 mesh three times, capsuled into No. 3.

The following examples related to the pharmaceutical experiments. The results were presented as mean±S.E.M using SPSS 13.0 for windows. Data were analyzed by means of one-way ANOVA for abdominal constriction test and formalin test or repeated-measures, and ANOVA for the hot-plane test and tail-swing test followed by least significant difference test. Statistical significance was indicated by P values <0.05.

EXAMPLE 36

Analgesic Screening Tests of the Compounds of the Invention

Evaluation on the analgesic activities of the representative compounds of the invention by the following tests 1. Experimental Method (Acetic Acid-Induced Writhing Test)

Kunming mice, male and female in half, were randomly divided into groups with 8 mice in each group. The following groups were established: the normal saline (NS) control group, in which normal saline was administered by subcutaneous injection (s.c.); the test groups, in which 31.0 umol/kg quaternary ammonium salts compounds of piperazines of the present invention was administered by s.c. All drugs were dissolved in normal saline before use. The drug was injected at the dose of 0.1 ml/10 g. After 30 min, 0.2 ml of 0.6% acetic acid was injected intraperitoneally for each mouse. After 2~3 min, the writhing reactions such as abdominal constriction, stretch of body and hind limbs, and hip raise occurred. Five minutes after acetic acid injection, the numbers of writhing was counted for 10 min. The percentage of inhibition was determined by using the following formula (1):

$$\text{Inhibition \%} = [(\text{The numbers of writhing of control group} - \text{the numbers of writhing of drag injection group})/\text{the numbers of writhing of control group}] \times 100\% \quad (1)$$

2 Experimental Results

The analgesic activities of the representative quaternary ammonium salt compounds of spirocyclomonopiperazines on the pain induced by acetic acid were shown in Table 1.

TABLE 1

The analgesic activities of the representative quaternary ammonium salt compounds of spirocyclomonopiperazines on the pain induced by acetic acid

| Nos. | Compounds | Mice (Numbers) | Inhibition(%) |
|---|---|---|---|
| Normal Saline Control group | NS | 8 | 0 |
| 6 | LXM-6 | 8 | 30 |
| 8 | LXM-8 | 8 | 55 |
| 9 | LXM-9 | 8 | 62 |
| 10 | LXM-10 | 8 | 65 |
| 11 | LXM-11 | 8 | 44 |
| 16 | LXM-16 | 6 | 61 |
| 18 | LXM-18 | 6 | 20 |
| 19 | LXM-19 | 8 | 56 |
| 20 | LXM-20 | 8 | 53 |
| 21 | LXM-21 | 8 | 47 |
| 22 | LXM-22 | 8 | 56 |
| 23 | LXM-23 | 8 | 39 |
| 24 | LXM-24 | 8 | 46 |
| 25 | LXM-25 | 8 | 37 |
| 28 | LXM-28 | 8 | 49 |
| 30 | LXM-30 | 8 | 43 |
| 31 | LXM-31 | 8 | 58 |

EXAMPLE 37

Pharmaceutical Experiments of LXM-10

Compound LXM-10 was used as a probe to further investigate their analgesic activities and mechanism of the compounds of this invention by multiple experimental methods. The results are shown below:

(I) The Hot-Plane Test

1. Experimental Method

The temperature of the hot-plate was adjusted to 55° C. With licking hind paws and jumping as observation index, the time from placing of the animal on the hot plate to observation the above reactions was recorded as latency time, Latency time was measured for three times and calculated their mean value as Basal threshold or Baseline latency (BL), Mice with latency time of less than 5 s or more than 10 s were eliminated from the study. The remaining mice were divided into 8 groups, and 10 mice in each group. The following groups were established: the normal saline control group (NS), in which normal saline was administered (s.c.); the morphine control group (Mor), in which morphine was administered (s.c.) at the dose of 10.0 mg/kg; and compound LXM-10 groups, in which compound LXM-10 were administered (s.c.) at the dose of 0.75, 1.5, 3.0, 6.0, 12.0 and 24.0 mg/kg. All drugs were dissolved in normal saline before use. The drugs injected at the dose of 0.1 ml/10 g. The latency times were measured at 1.0, 1.5, 2.0, and 3.0 h after administering LXM-10. The cut-off time was set at 30 s to avoid skin scald. The percentage of pain threshold elevated rate (PTE %) was determined by using the following formula (2):

PTE %=(The latency time of drug injection group−the latency time of control group at the corresponding time point)/the latency time of control group at the corresponding time point×100%     (2)

To judge whether LXM-10 was effective as analgesic using this criterion: at the peak time point of this compound, the latency times of each compound LXM-10 group was greater than the mean latency time of normal saline control group at the corresponding time point plus three times of standard deviation. The effective percentage of each group was calculated made data conversion, then calculated the analgesic $ED_{50}$ and 95% confidence interval (CI) in accordance with the formulae (3) and (4) using General Method for Calculating.

$$ED_{50} = lg^{-1}[Xm - i(\Sigma P - 0.5)] \quad (3)$$

$$95\% \; CI \; of \; ED_{50} = lg^{-1}(lgED_{50} \pm 1.96S) \quad (4)$$

$$S = i\sqrt{\frac{\Sigma P - \Sigma P_1}{n-1}}$$

Wherein, Xm represents the logarithm value of the largest dose, i refers to group interval, $\Sigma P$ refers to the sum of each group's efficiency, $\Sigma P^2$ represents the square sum of each group's efficiency, n refers to numbers of experimental groups.

2. Experimental Results

The experimental results were shown in FIG. 1. *P<0.05, **P<0.01 were recorded by comparison with normal saline control group. The onset time of LXM-10 is at 1.0 h peaked at 2.0 h, and persisted to 3.0 h. The percentage of pain threshold elevated rates were 47.5%, 54.8%, 79.2%, and 126.8% respectively at 1.5, 3.0, 6.0, and 12.0 mg/kg at 2.0 h, and showed a dose-effect relationship to some extent. $ED_{50}$ value is 3.2 mg/kg with (1.8~5.4) mg/kg at a 95% confidence interval.

(II) Acetic Acid-Induced Writhing Test

1. Experimental Method

This experiment was carried out according to that of Example 36.

2. Experimental Results

Figure 2:
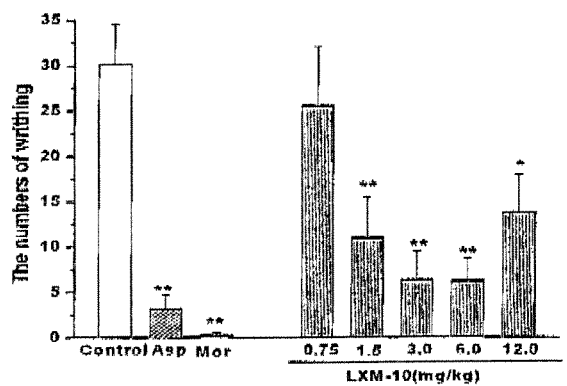
FIG. 2. Analgesic activity of LXM-10 in writhing test induced by acetic acid.

The experimental results were shown in FIG. 2, *P<0.05, P<0.01 were recorded by comparison with normal saline control group. As shown in FIG. 2**, the percentage of pain inhibition were 63.4%, 78.8%, 79.2% and 55.6% with 1.5, 3.0, 6.0 and 12.0 mg/kg at 0.5 h after s.c. administration, and showed a dose-effect relationship to some extent.

(III) Formalin Test

1. Experimental Method

Sixty ICR mice, male and female in half, were divided into six groups with 10 mice in each group. The following groups were established: the normal saline (NS) control group, in which normal saline was administered by s.c.; the aspirin control group, in which aspirin was administered by i.g. at the dose of 300 mg/kg; the morphine control, group, in which morphine was administered (s.c.) at the dose of 10.0 mg/kg; and compound LXM-10 groups, in which compound LXM-10 were administered (s.c.) at the dose of 0.75, 1.5, 3.0 and 6.0 mg/kg. All drugs were dissolved in normal saline before use. The drugs injected at the dose of 0.1 ml/10 g. 30 min after administration, animals were administered 20 ul of 2.5% formalin solution on the right front paws. The licking times were recorded immediately in the duration of 0~5 minutes as phase I reaction; After 20 minutes, the licking times were recorded in the duration of 20~25 minutes as phase II reaction. The percentage of pain inhibition (%) was determined by using the following formula (5):

Pain inhibition %=[(The licking time of normal saline control group−the licking time of drug injection group)/the licking time of normal saline control group]×100%     (5)

2. Experimental Results

Figure 3:
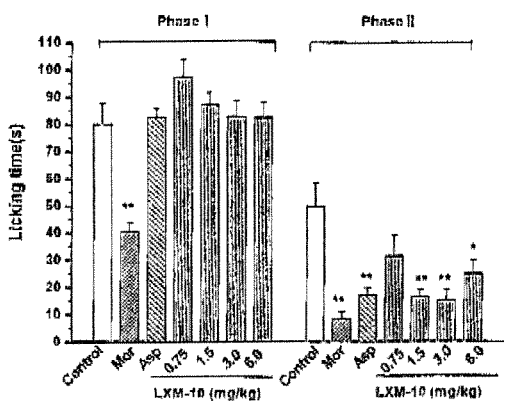
FIG. 3, Analgesic activity of LXM-10 in formalin-induced pain.

The effect of LXM-10 on formalin-induced pain was shown in FIG. 3. 0.5 h after administering LXM-10 (s.c.), no obvious effect of LXM-10 on the licking time in Phase I was observed. But the licking time in Phase II was significantly reduced. The percentage of pain inhibitions were 67.0%, 69.6% and 50.0% respectively, and showed a dose-effect relationship to some extent.

Wherein, *P<0.05, **P<0.01 were recorded by random comparison between any one of normal saline group/NS group/normal saline group.

EXAMPLE 38

Mechanism Studies on the Analgesic Activities of the Compounds

Compound LXM-10 was used as a probe to explore the mechanism by means of the hot-plate test mentioned above.

1. Effect of LXM-10 on Opiate Receptors

Figure 4:
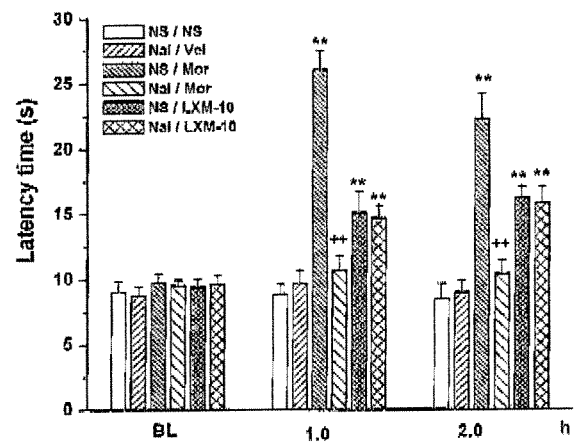
FIG. 4. Effect of Naloxone on the analgesic effect of LXM-10.

The effect of naloxone (Nal) on the analgesic activities of LXM-10 was shown in FIG. 4. The results showed that, the analgesic effect of LXM-10 was not blocked by naloxone, which indicated that the analgesic activities of LXM-10 independent of opioid receptors. In FIG. 4, "Vel" represents normal saline group; BL represents basal latency time; **P<0.01 were recorded by comparison between NS/NS group at the corresponding time point, while ++P<0.01 were recorded by comparison between NS group/Mor group at the corresponding time point.

2. Effect of LXM-10 on Nicotinic Receptors

Figure 5:
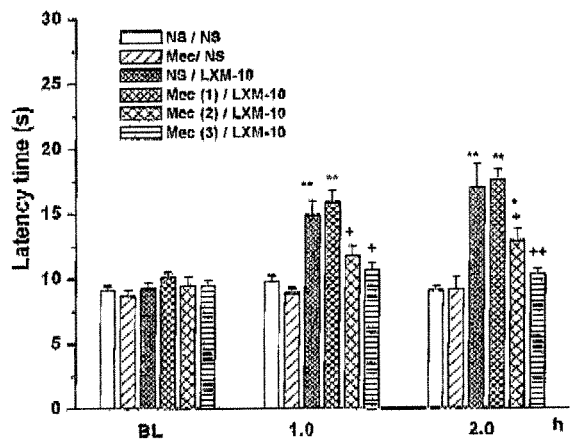
FIG. 5. Effect of mecamylamine on the analgesic effect of LXM-10 in hot-plate test.
Figure 6:
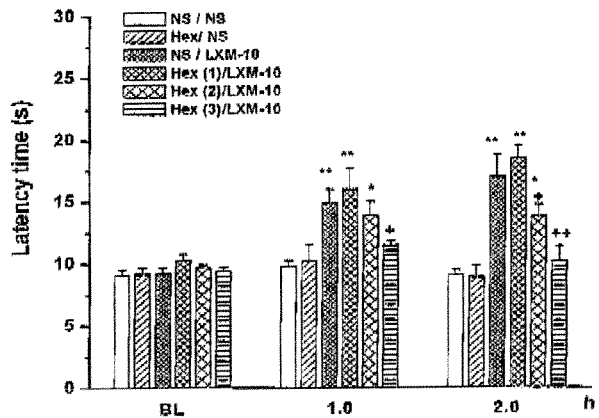
FIG. 6, Effect of hexamethonium on the analgesic effect of LXM-10 in hot-plate test.

The effects of mecamylamine (Mec) and hexamethonium (Hex) on the analgesic activities of LXM-10 was shown in FIG. 5 and FIG. 6. The results showed that the analgesic effect of LXM-10 was blocked by mecamylamine and hexamethonium in a dose-dependent manner, which indicated that the analgesic activities of LXM-10 dependent of agonising peripheral nicotinic receptors. In FIG. 5, BL represents basal latency time; Mec(1), Mec(2) and Mec(3) represent different experimental results of three different doses (1.0, 2.5 and 5.0 mg/kg). *P<0.05, **P<0.01 were recorded by comparison between NS/NS group at the corresponding time point, while +P<0.05 and ++P<0.05 were recorded by comparison between NS/LXM-10 group at the corresponding time point.

In FIG. 6, BL represents basal latency time; Mec(1), Mec(2) and Mec(3) represent different experimental results of three experimental doses (1.0, 2.5 and 5.0 mg/kg). *P<0.05, **P<0.01 were recorded by comparison between NS/NS group at the corresponding time point, while +P<0.05 and ++P<0.05 were recorded by comparison between NS/LXM-10 group at the corresponding time point.

3. Effect of LXM-10 on Muscarine Receptors

Figure 7:
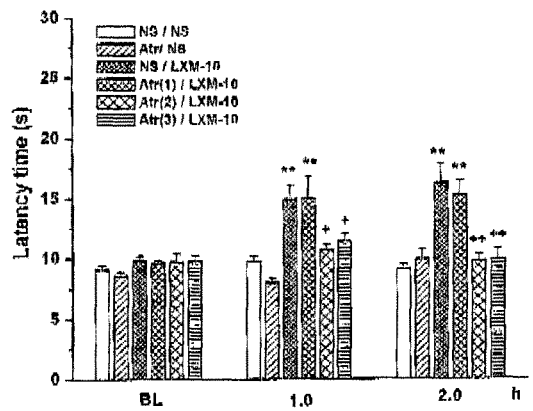
FIG. 7. Effect of atropine on the analgesic effect of LXM-10 in hot-plate test.
Figure 8:
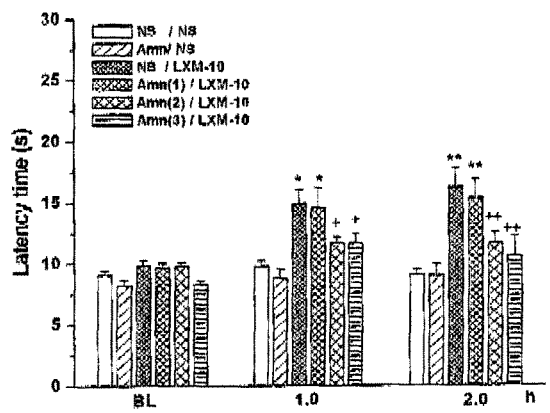
FIG. 8. Effect of atropine methylnitrate on the analgesic effect of LXM-10 in hot-plate test.

The effects of atropine (Atr) and methyl atropine (Amn) on the analgesic activities of LXM-10 shown in FIG. 7 and FIG. 8. The results showed that the analgesic effect of LXM-10 was blocked by atropine and methyl atropine in a dose-dependent manner, which indicated that the analgesic activities of LXM-10 was dependent of peripheral muscarine receptors. In FIG. 7, BL represents basal latency time; Atr(1), Atr(2) and Atr(3) represent different experimental results of three different doses (1.0, 2.5 and 5.0 mg/kg). *P<0.05, P<0.01 were recorded by comparison between NS/NS group at the corresponding time point, while +P<0.05 and ++P<0.05 were recorded by comparison between NS/LXM-10 group at the corresponding time point. In FIG. 8**, BL represents basal latency time; Amn(1), Amn(2) and Amn(3) represent different experimental results of three different doses (1.0, 2.5 and 5.0 mg/kg). *P<0.05. **P<0.01 were recorded by comparison between NS/NS group at the corresponding time point, while +P<0.05 and ++P<0.05 were recorded by comparison between NS/LXM-10 group at the corresponding time point.

4. Effect of LXM-10 on $\alpha_2$-Adrenergic Receptor

Figure 9:
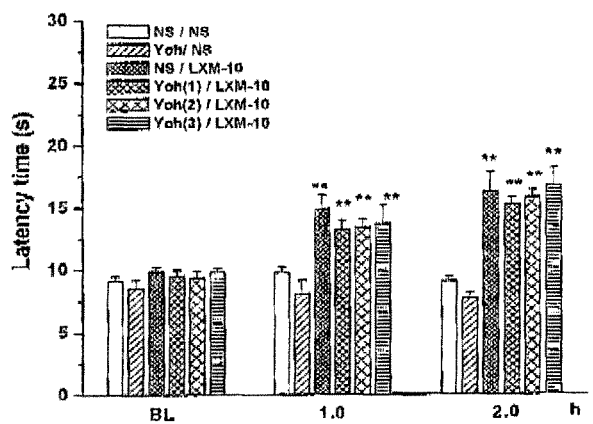
FIG. 9. Effect of Yohimbine on the antinociceptive effect of LXM-10 in hot-plate test.

The effect of yohimbine (Yoh) on the analgesic activities of LXM-10 was shown in FIG. 9. The results showed that the analgesic effect of LXM-10 was not blocked by yohimbine, which indicated that the analgesic activities of LXM-10 independent of $\alpha_2$-adrenergic receptors.

In FIG. 9, BL represents basal latency time; Yoh(1), Yoh(2) and Yoh(3) represent different different experimental results of three different doses (1.0, 2.5 and 5.0 mg/kg). **P<0.01 were recorded by comparison between NS/NS group at the corresponding time point.

EXAMPLE 39

Evaluation on Toxic- and Side-Effects of LXM-10

All the following tests were carried out by using compound LXM-10 according to the routine methods.

1. Addiction Test of Compound LXM-10

Using compound LXM-10 as test compound, mice showed no tail-erected response at the doses of 6.0, 12.0, 24.0 or 445.0 mg/kg, respectively. They are quiet and normal.

2. Acute Toxicity Test on LXM-10

$LD_{50}$ value of compound LXM-10 is 514.0 mg/kg (sc) with (495.4-530.8) mg/kg at a 95% confidence interval.

3. Effect of LXM-10 on the Function of Motion Coordination in Mice

As shown in Table 2, compound LXM-10 did not significantly affect tire function of motion coordination in mice. The effect of muscle-relaxed effect on the analgesic effect of LXM-10 was also excluded.

TABLE 2

Effect of LXM-10 on function of motion coordination in mice

| Groups | Doses (mg/kg) | Before treatment (s) | Time of falling down from rota-rod after treatment (s) | | |
|---|---|---|---|---|---|
| | | | 0.5 h | 2.0 h | 3.5 h |
| NS | — | 95.4 ± 8.48 | 118.1 ± 1.87 | 119.5 ± 0.38 | 119.3 ± 0.62 |
| Diazepam | 2.0 | 102.5 ± 6.48 | 48.8 ± 14.0** | 73.3 ± 14.1** | 111.7 ± 6.70 |
| LXM-10 | 6.0 | 96.7 ± 9.17 | 106.5 ± 8.88 | 110.0 ± 5.17 | 116.2 ± 3.75 |
| | 12.0 | 96.6 ± 8.93 | 109.6 ± 10.3 | 109.3 ± 8.15 | 119.6 ± 0.38 |
| | 24.0 | 101.2 ± 9.15 | 112.7 ± 5.18 | 117.5 ± 2.50 | 119.0 ± 1.00 |

**P < 0.01, compared with normal saline control group (NS).

4. Effect of LXM-10 on the Spontaneous Motion in Mice

As shown in Table 3, compound LXM-10 did not significantly affect spontaneous motion in mice.

TABLE 3

Effect of LXM-10 on the spontaneous motion in mice

| Groups | Doses (mg/kg) | Before treatment | Numbers of movement after treatment | | |
|---|---|---|---|---|---|
| | | | 0.5 h | 2.0 h | 3.5 h |
| NS | | 45.3 ± 2.53 | 40.2 ± 2.51 | 41.6 ± 2.42 | 41.5 ± 4.00 |
| Diazepam | 2.0 | 51.5 ± 5.15 | 5.37 ± 1.64** | 10.8 ± 3.10** | 18.2 ± 3.61* |
| LXM-10 | 6.0 | 46.8 ± 1.96 | 46.6 ± 2.63 | 42.3 ± 3.38 | 48.0 ± 5.00 |
| | 12.0 | 47.7 ± 2.55 | 48.0 ± 6.21 | 48.1 ± 6.14 | 48.0 ± 7.85 |
| | 24.0 | 50.2 ± 2.31 | 43.5 ± 4.21 | 45.5 ± 6.05 | 46.6 ± 3.69 |

TABLE 3-continued

Effect of LXM-10 on the spontaneous motion in mice

| Groups | Doses (mg/kg) | Before treatment | Numbers of movement after treatment | | |
|---|---|---|---|---|---|
| | | | 0.5 h | 2.0 h | 3.5 h |

*P < 0.05,
**P < 0.01, compared with normal saline control group (NS).

5. Effect of LXM-10 on the Body Temperature in Mice

As shown in Table 4, compound LXM-10 did not affect body temperature in mice.

TABLE 4

Effect of LXM-10 on the body temperature in mice

| Groups | Doses (mg/kg) | Before treatment | Rectal temperature after treatment (° C.) | | |
|---|---|---|---|---|---|
| | | | 0.5 h | 2.0 h | 3.5 h |
| NS | — | 37.1 ± 0.18 | 37.4 ± 0.25 | 37.1 ± 0.25 | 37.1 ± 0.21 |
| Diazepam | 2.0 | 37.6 ± 0.17 | 35.1 ± 0.26** | 35.9 ± 0.35** | 36.5 ± 0.31 |
| LXM-10 | 6.0 | 37.7 ± 0.34 | 37.3 ± 0.35 | 37.3 ± 0.28 | 37.5 ± 0.29 |
| | 12.0 | 37.1 ± 0.09 | 37.0 ± 0.26 | 37.1 ± 0.24 | 37.1 ± 0.20 |
| | 24.0 | 37.0 ± 0.18 | 37.5 ± 0.21 | 37.0 ± 0.19 | 37.3 ± 0.16 |

*P < 0.05,
**P < 0.01, compared with normal saline control group (NS).

The following conclusions were drawn from the above results:
- the compound LXM-10 produced obvious analgesic activity in chemical-induced and thermal-induced pain in a dose-dependent and time-dependent manner;
- The analgesic activity of LXM-10 was dependent of agonising peripheral nicotinic receptors and muscarine receptors;
- The analgesic activity of LXM-10 was independent of opioid receptors or $\alpha_2$-adrenergic receptor, which would avoid the addiction or some adverse reactions;
- LXM-10 did not show obvious toxic- and side-effects; it has not addition and did not significantly affect motion coordination, spontaneous motion and body temperature in mice;
- Based on the mechanism study on the LXM-10, we propose that an acting site F possibly exists in peripheral system, and agonising nicotinic receptors and muscarine receptors simultaneously are required to produce analgesic activity of LXM-10.

From the above conclusions, it can be deduced that quaternary ammonium salts compounds of spirocyclomonopiperazine represented by LXM-10 showed definite analgesic activity. Their mechanism is novel. These compounds have low toxic- and side-effect and no addiction. Therefore, it can be expected that these compounds will be developed into new analgesics with no addiction.

The invention claimed is:

1. The compounds represented by general formula (I):

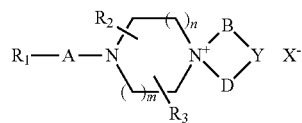

I or their stereoisomers, tautomers, pharmaceutically acceptable salts, wherein, $R_1$ is substituted or unsubstituted phenyl;

A is a bond, or a $C_2$-$C_3$ saturated straight-chain alkylene, or branched-chain or straight-chain alkenylene with 3 carbon atoms in straight-chain part;

$R_2$, $R_3$ are each independently hydrogen or methyl which is linked to any position of spirocyclo-structure;

n and m are each independently an integer between 0-2, wherein m and n are not zero simultaneously;

B and D are each independently $C_1$ straight-chain, $C_3$ straight-chain, or $C_1$-$C_3$ branched-chain alkylene;

Y is O; and $X^-$ is pharmaceutically acceptable organic or inorganic anion, with the proviso that when A is a bond, the cycle structure composed of D, N, B and Y is not unsubstituted five-numbered ring.

2. The compound according to claim 1, wherein when $R_1$ is substituted or unsubstituted phenyl with one or more substitutents; the substituents are selected from a group consisting of halogen, amino, hydroxyl, cyano, nitro, alkyl, alkoxy and alkoxycarbonyl; in which the alkyl or alkoxy is straight-chain or branched-chain group with 1-6 carbon atoms, the alkoxycarbonyl is the group with total carbon atoms of 2-6.

3. The compound according to claim 1, wherein when $R_1$ is a substituted or unsubstituted heteroaryl, the heteroaryl is a five- or six-numbered ring with 1-4 hetero-atoms selected from N, O and S.

4. The compound according to claim 1, wherein when $R_1$ is a substituted or unsubstituted heteroaryl, said A is a bond.

5. The compound according to claim 1, wherein the $R_1$ group is p-methylphenyl, p-methoxyphenyl, p-nitrophenyl, m-nitrophaenyl, p-chlorophenyl, o-methylphenyl, o-fluorophenyl, m-fluorophenyl, m-hydroxyphenyl, m-cyanophenyl, m-ethoxycarbonyl-phenyl, m-methoxycarbonyl-phenyl, m-aminophenyl, or o-nitrophenyl.

6. The compound according to claim 1, wherein both m and n are 1; B and D are each independently selected from a group consisting of —$CH_2$—, —$(CH_2)_3$—, —$CH(CH_3)$—, —$CH_2CH_2CH_2$— and —$CH_2CH(CH_3)$—; Y is —O—; $X^-$ is halide anion.

7. The compound according to claim 3, wherein R1 is selected from the group consisting of pyridyl, pyrazinyl, pyrazolyl, pyrimidinyl, pyridazinyl, and pytiridyl.

8. The compound according to claim 6, wherein X⁻ is selected from a chloride anion and a bromide anion.

9. The compound according to claim 1, wherein the compounds are:
- 2,4-dimethyl-9-β-(p-nitrophenyl)ethyl-3-oxo-6,9-diazaspiro[5.5]undecane chloride;
- 2,4-dimethyl-9-β(p-methoxyphenyl)ethyl-3-oxo-6,9-diazaspiro[5.5]undecane chloride;
- 2,4-dimethyl-9-β-(m-fluorophenyl)ethyl-3-oxo-6,9-diazaspiro[5.5]undecane chloride;
- 2,4-dimethyl-9β-phenylethyl-3-oxo-6,9-diazaspiro[5.5]undecane chloride;
- 2,4-dimethyl-9-γ-phenylpropyl-3-oxo-6,9-diazaspiro[5.5]undecane chloride;
- 2,4-dimethyl-9-cinnamyl-3-oxo-6,9-diazaspiro[5.5]undecane chloride; and
- 2,4,7-trimethyl-9-β-phenylethyl-3-oxo-6,9-diazaspiro[5.5]undecane chloride.

10. A compound having the following structural formula:

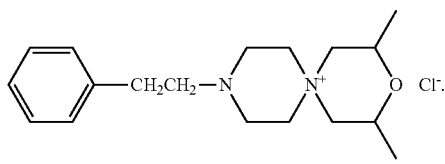

11. An analgesic pharmaceutical composition comprising a compound according to claim 1, wherein the composition comprises the compound of formula (I), their stereoisomers, tautomers, prodrugs, pharmaceutical acceptable salts as active component, and optionally containing pharmaceutically acceptable carriers.

12. A process for preparing the compound according to claim 1, the process includes:
(1) in the presence of catalyst, compound (A) is reacted with compound (B) in solvent under 40~140° C. to produce compound (C), wherein the solvent is selected from a group consisting of alcohols, ketones, nitriles, chlorohydrocarbons, benzene series solvents, DMSO and DMF; the catalyst is inorganic bases or organic bases:

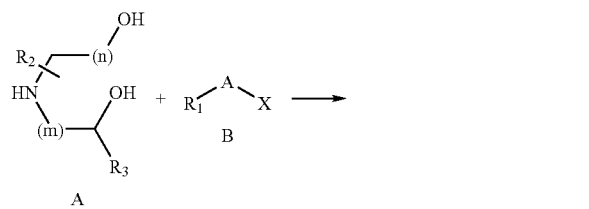

(2) chlorating the obtained product (C) at the temperature of 0-80° C. to give Compound (D), wherein the solvent used in chloration is non-protonic solvents, and the chlorating reagent used is selected from the group consisting of thionyl chloride, phosphorus trichloride and phosphoric pentachloride:

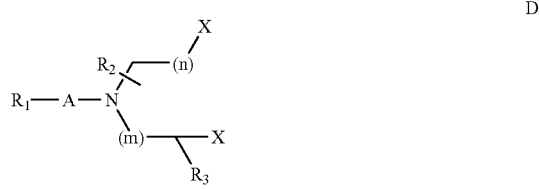

(3) in the presence of catalyst, the compound (D) is reacted with compound (E) to produce the target compound (I) in a solvent under 40-140° C.:

wherein the solvent is selected from the group consisting of alcohols, ketones, nitriles, chlorohydrocarbons, benzene series solvents, DMSO and DMF; the catalyst is inorganic bases or organic bases.

13. The process according to claim 12, wherein in steps (1) and (3), the reaction temperature is at 80° C.; the solvent used is selected from a group consisting of methanol, ethanol, isopropanol, acetonitrile, acetone, toluene, benzene, DMSO, DMF, chloroform, dichloromethane and glycol, preferably ethanol; the catalyst is inorganic base selected from a group consisting of oxides, hydroxides, carbonates, and bicarbonates of alkali metals or alkaline-earth metals, or organic base selected from a group consisting of triethylamine and isopropanolamine; and in step (2), the solvent is chloroform, the chlorating agent is thionyl chloride, and the reaction temperature is at 50° C.

14. A process for preparing the compound according to claim 1, the process includes:
(1) in the presence of catalyst, compound (F):

is reacted with compound (B) of R1-A-X in a solvent to produce intermediate compound (G); when R1-A-X is non-aromatic halide, the reaction temperature is at 40~140° C., the solvent is selected from a group consisting of alcohols, ketones, nitriles, chloro-hydrocarbons, benzene series solvents, DMSO and DMF, and the catalyst is various inorganic bases or organic bases; when R1-A-X is aromatic halide, the reaction temperature is at −20~140° C., the solvent is protonic solvents, the catalyst is selected from a group consisting of cuprous iodide, cuprous chloride, cuprous bromide and cuprous oxide, an inorganic base is simultaneously added, the inorganic bases selected from a group consisting of potassium phosphate, potassium carbonate, sodium carbonate, sodium dicarbonate and sodium hydroxide:

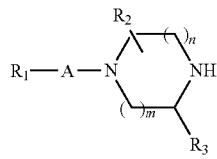  G (2) In the presence of catalyst, the obtained compound (G) is reacted with compound (H):

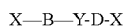—B—-D-X  H at the temperature of 40~140° C. in solvent to provide the target compound (I); wherein the solvent is selected from a group consisting of alcohols, ketones, nitriles, chlorohydrocarbons, benzene series solvents, DMSO and DMF; and the catalyst used is inorganic bases or organic bases.

15. A process according to claim 14, wherein, in step (I), when compound (B) is non-aromatic halide, the solvent is selected from a group consisting of methanol, ethanol, isopropanol, acetonitrile, acetone, toluene, benzene, DMSO, DMF, chloroform and dichloromethane; the catalyst is inorganic base selected from a group consisting of oxides, hydroxides, carbonates, and bicarbonates of alkali metals or alkaline-earth metals, or organic base selected from triethylamine or iso-propanolamine, the reaction temperature is at 80° C.; when compound (B) is aromatic halide, the protonic solvent is selected from a group consisting of methanol, ethanol, propanol, isopropanol, glycol and glycerol; the catalyst is cuprous iodide, and potassium phosphate is added simultaneously; and wherein, in step (2), the solvent is selected from a group consisting of methanol, ethanol, isopropanol, acetonitrile, acetone, toluene, benzene, DMSO, DMF, chloroform, dichloromethane and glycol; the catalyst is inorganic base selected from oxides, hydroxides, carbonates, and dicarbonates of alkali metals or alkaline-earth metals, or organic base selected from triethylamine or isopropanolamine, the reaction temperature is at 80° C.

16. The process according to claim 13, wherein in steps (1) and (3), the solvent used is ethanol; the catalyst is sodium carbonate in step (1) and sodium bicarbonate in step (3) respectively.

17. A process according to claim 15, wherein, in step (I), when compound (B) is non-aromatic halide, the solvent is ethanol, the catalyst is sodium carbonate; when compound (B) is aromatic halide, the protonic solvent is isopropanol; and wherein, in step (2), the solvent is ethanol; the catalyst is sodium dicarbonate.

* * * * *